US009683000B2

(12) United States Patent
Muhammad et al.

(10) Patent No.: US 9,683,000 B2
(45) Date of Patent: Jun. 20, 2017

(54) CARBONATE PRODRUGS AND METHODS OF USING THE SAME

(71) Applicant: Acorda Therapeutics, Inc., Ardsley, NY (US)

(72) Inventors: Naweed Muhammad, Fremont, CA (US); Keith R. Bley, Menlo Park, CA (US)

(73) Assignee: Acorda Therapeutics, Inc., Ardsley, NY (US)

( * ) Notice: Subject to any disclaimer, the term of this patent is extended or adjusted under 35 U.S.C. 154(b) by 0 days.

(21) Appl. No.: 15/017,329

(22) Filed: Feb. 5, 2016

(65) Prior Publication Data

US 2017/0008916 A1 Jan. 12, 2017

Related U.S. Application Data

(60) Continuation of application No. 14/629,324, filed on Feb. 23, 2015, now Pat. No. 9,289,501, which is a continuation of application No. 14/252,683, filed on Apr. 14, 2014, now Pat. No. 8,993,545, which is a division of application No. 12/993,089, filed as application No. PCT/US2009/044746 on May 20, 2009, now Pat. No. 8,735,376.

(60) Provisional application No. 61/054,765, filed on May 20, 2008.

(51) Int. Cl.
C07F 9/09 (2006.01)
C07F 9/11 (2006.01)
C07C 233/25 (2006.01)
A61K 31/661 (2006.01)
A61K 47/48 (2006.01)

(52) U.S. Cl.
CPC ............ C07F 9/096 (2013.01); A61K 31/661 (2013.01); A61K 47/48084 (2013.01); C07C 233/25 (2013.01); C07F 9/11 (2013.01)

(58) Field of Classification Search
None
See application file for complete search history.

(56) References Cited

U.S. PATENT DOCUMENTS

| | | | |
|---|---|---|---|
| 4,322,410 A | 3/1982 | Stjepanovic et al. |
| 5,001,115 A | 3/1991 | Sloan |
| 5,073,641 A | 12/1991 | Bundgaard et al. |
| 5,272,171 A | 12/1993 | Ueda et al. |
| 5,498,729 A | 3/1996 | Domb |
| 5,939,405 A | 8/1999 | Starrett, Jr. et al. |
| 5,985,856 A | 11/1999 | Stella et al. |
| 6,043,285 A | 3/2000 | Pinza et al. |
| 6,140,310 A | 10/2000 | Glazier |
| 6,204,257 B1 | 3/2001 | Stella et al. |
| 6,214,811 B1 | 4/2001 | Glazier et al. |
| 6,362,172 B2 | 3/2002 | Ueda et al. |
| 6,451,776 B2 | 9/2002 | Stella et al. |
| 6,713,089 B1 | 3/2004 | Bertelsen et al. |
| 6,825,204 B2 | 11/2004 | Liu |
| 6,872,838 B2 | 3/2005 | Stella et al. |
| 6,916,825 B2 | 7/2005 | Senn-Bilfinger et al. |
| 7,230,005 B2 | 6/2007 | Shafer et al. |
| 7,244,718 B2 | 7/2007 | Stella et al. |
| 8,735,376 B2 | 5/2014 | Muhammad et al. |
| 8,993,545 B2 | 3/2015 | Muhammad et al. |
| 9,289,501 B2 | 3/2016 | Muhammad et al. |
| 2002/0090398 A1 | 7/2002 | Dunn et al. |
| 2003/0022876 A1 | 1/2003 | Ashton et al. |
| 2004/0058946 A1 | 3/2004 | Buchwald et al. |
| 2004/0186081 A1 | 9/2004 | Slusher et al. |
| 2005/0020576 A1 | 1/2005 | Zhang et al. |
| 2005/0026850 A1 | 2/2005 | Robinson et al. |
| 2005/0026879 A1 | 2/2005 | Robinson et al. |
| 2005/0080260 A1 | 4/2005 | Mills et al. |
| 2005/0147668 A1 | 7/2005 | Bertelsen et al. |
| 2006/0089383 A1 | 4/2006 | Le Bourdonnec et al. |
| 2006/0116422 A1 | 6/2006 | De Groot et al. |
| 2007/0042999 A1 | 2/2007 | West et al. |
| 2008/0318905 A1 | 12/2008 | Muhammad et al. |
| 2010/0234452 A1 | 9/2010 | Mian et al. |
| 2011/0212926 A1 | 9/2011 | Muhammad et al. |
| 2011/0263545 A1 | 10/2011 | Muhammad et al. |
| 2014/0243407 A1 | 8/2014 | Bley et al. |

FOREIGN PATENT DOCUMENTS

| | | |
|---|---|---|
| WO | WO-00/08033 A1 | 2/2000 |
| WO | WO-01/52852 A1 | 7/2001 |
| WO | WO-2005/077394 A1 | 8/2005 |
| WO | WO-2006/014282 A2 | 2/2006 |

(Continued)

OTHER PUBLICATIONS

Mantyla et al., A novel synthetic route for the preparation of alkyl and benzyl chloromethyl phosphates, 2002, Tetrahedron Letters, 43, 3793-3794.*

Vigroux et al., Synthesis of Prodrugs and a Mutual Prodrug of Chlorzoxazone and Acetaminophen Based on a Masked Benzoxazolone, 1995, Bioorganic & Medicinal Chemistry Letters, vol. 5, No. 5, 427-430.*

Baliga, S.S. (May 2009). "Acetaminophen Confers Neuroprotection During Early Cerebral Ischemia-Reperfusion," *A Dissertation submitted to the Graduate School-New Brunswick Rutgers, The State University of New Jersey and the Graduate School of Biomedical Sciences University of Medicine and Dentistry and Dentistry of New Jersey*, 125 pages.

Berenblum, I. et al. (1959). "Skin-Initiating Action and Lung Carcinogenesis by Derivatives of Urethane (Ethyl Carbamate) and Related Compounds," *Biochemical Pharmacology* 2:168-176.

(Continued)

*Primary Examiner* — Kristin Vajda
(74) *Attorney, Agent, or Firm* — Morrison & Foerster LLP

(57) ABSTRACT

The present invention provides carbonate prodrugs which comprise a carbonic phosphoric anhydride prodrug moiety attached to the hydroxyl or carboxyl group of a parent drug moiety. The prodrugs may provide improved physicochemical properties over the parent drug. Also provided are methods of treating a disease or condition that is responsive to the parent drug using the carbonate prodrugs, as well as kits and unit dosages.

1 Claim, 3 Drawing Sheets

(56) References Cited

FOREIGN PATENT DOCUMENTS

| WO | WO-2006/014282 A3 | 2/2006 |
|----|-------------------|--------|
| WO | WO-2009/143295 A1 | 11/2009 |
| WO | WO-2009/143297 A1 | 11/2009 |
| WO | WO-2009/143299 A1 | 11/2009 |
| WO | WO-2010/030781 A2 | 3/2010 |
| WO | WO-2010/030781 A3 | 3/2010 |
| WO | WO-2013/044064 A1 | 3/2013 |

OTHER PUBLICATIONS

De Jong, R.S. et al. (1997). "Randomized comparison of etoposide pharmacokinetics after oral etoposide phosphate and oral etoposide" *British Journal of Cancer*, 75(11), 1660-1666.
Extended European Search Report mailed on Mar. 27, 2012, for EP Patent Application No. 09751525.8, filed on May 20, 2009, 7 pages.
FDA Anesthetic and Life Support Drugs Advisory Committee (May 7, 2008). "AQUAVAN® (Fospropofol Disodium) Injection," Web Slide Presentation, 150 pages.
Grosios, K. et al. (1999). "In Vivo and in Vitro Evaluation of Combretastatin A-4 and its Sodium Phosphate Prodrug", *British Journal of Cancer*, 81(8):1318-1327.
"Guidelines and Practice of the Foundation Learning in Nursing," (Apr. 30, 2007). First Edition, P. Kaiyuan ed., *Second Military Medical University Press*, p. 28.
Hadzimichalis, N.M. et al. (Dec. 2007, e-pub. Oct. 5, 2007). "Acetaminophen-Mediated Cardioprotection via Inhibition of the Mitochrondrial Permeability Transition Pore-Induced Apoptotic Pathway," *Am. J. Physiol. Heart Circ. Physiol.* 293:H3348-H3355.
International Search Report mailed on Jul. 7, 2009, for PCT Patent Application No. PCT/US09/44746, filed on May 20, 2009, 1 page.
International Search Report mailed on Jul. 16, 2009, for PCT Patent Application No. PCT/US09/44743, filed on May 20, 2009, 1 page.
International Search Report mailed on Dec. 3, 2012, for PCT Patent Application No. PCT/US2012/056625, internationally filed on Sep. 21, 201, 3 pages.
Mayo Clinic (updated Jul. 13, 2013). "Myocardial Ischemia Prevention," located at http://www.mayoclinic.com/health/myocardial-ischemia/DS01179/DSECTION=prevention, last visited on Oct. 29, 2013, two pages.
Kazlauskas, R.J. et al. (1985). "Synthesis of Methoxycarbonyl Phosphate, a New Reagent Having High Phosphoryl Donor Potential for Use in ATP Cofactor Regeneration," *J. Org. Chem.* 50:1069-1076.
Krise, J.P. et al. (Aug. 12, 1999, e-pub. Jul. 17, 1999). "Novel Prodrug Approach for Tertiary Amines: Synthesis and Preliminary Evaluation of N-Phosphonooxymethyl Prodrugs," *Journal of Medicinal Chemistry* 42(16):3094-3100.
Laird, B. et al. (May 2008, e-pub. Apr. 23, 2008). "Management of Cancer Pain: Basic Principles and Neuropathic Cancer Pain," *European Journal of Cancer* 44(8):1078-1082.
Lee, T. et al. (Oct. 2, 2006). "Solubility, Polymorphism, Crystallinity, and Crystal Habit of Acetaminophen and Ibuprofen by Initial Solvent Screening," *Pharmaceutical Technology*, located at <http://license.icopyright.net/user/viewFreeUse.act?fuid=MTI5NDI0MzY%3D>, last visited on May 26, 2011, 16 pages.
Mahara, J, H. et al. (2006, e-pub. Jul. 20, 2006). "Acetylsalicylic Acid and Acetaminophen Protect Against Oxidative Neurotoxicity," *Metabolic Brain Disease* 21(2-3):189-199.
Moller, P.L. et al. (2005). "Intravenous Acetaminophen (Paracetamol): Comparable Analgesic Efficacy, but Better Local Safety than Its Prodrug, Propacetamol, for the Postoperative Pain After Third Molar Surgery," *Anesth. Analg.* 101:90-96.
Moller, P.L. et al. (2005, e-pub. Mar. 24, 2005). "Onset of Acetaminophen Analgesia: Comparison of Oral and Intravenous Routes After Third Molar Surgery," *British Journal of Anaesthesia* 94(5):642-648.
Peeters, M.Y. et al. (Mar. 2006). "Propofol Pharmacokinetics and Pharmacodynamics for Depth of Sedation in Nonventilated Infants after MajorCraniofacial Surgery" *Anesthesiology* 104(3):466-74.
Poste, G. et al. (1976). "Lipid Vesicles as Carriers for Introducing Biologically Active Materials into Cells," Chapter 4 in *Methods in Cell Biology*, Prescott, D.M. ed., Academic Press, Inc.: New York, NY, XIV:33-71.
Rautio, J. et al. (2008). "Prodrugs: design and clinical applications", *Nature Reviews*, 7:255-270.
Roberts II, L.J. et al. (2001). "Analgesic-Antipyretic and Antiinflammatory Agents and Drugs Employed in the Treatment of Gout," Chapter 27 in *Goodman & Gillman's The Pharmacological Basis of Therapeutics*, 10th Edition, McGraw Hill, Medical Publishing Division: New York, NY, pp. 687-731.
Rowland, M. et al. (1995). "Variability" Chapter 13 in *Clinical Pharmacokinetics, Concepts and Applications*, Third Edition, p. 207.
Safadi, M. et al. "Phosphoryloxymethyl Carbamates and Carbonates—Novel water-soluble prodrugs for amines and hindered alcohols" *Pharmaceutical Research*, 10(9):1350-1355, 1993.
Sauer, R. et al. (2000). "Water-soluble Phosphate Prodrugs of I-Propargyl-8-styrylxanthine Derivatives, A2A-selective adenosine Receptor Antagonists", *J. Med. Chem.*, 43:440-448.
Shah et al., (2007). "Fospropofol Intravenous Injection for Procedural Sedation: A Population Pharmacokinetic Model" *Anesthesiology* 107:A45.
Stella, V.J. (2007). "Prodrug strategies to overcome poor water solubility", *Advanced Drug Delivery Reviews*, 59:(7) 677-694.
Taniguchi, M. et al. (1981). "Synthesis and Evaluation in Vitro of 4-Acetamidophenyl Phosphate", *Chemical and Pharmaceutical Bulletin*, 29(2): 577-580.
The China Food and Drug Administration. (Jan. 31, 2011). "CFDA Determines That the Pharmaceutical Preparation Comprising Dextropropoxyphene Will Withdraw From Domestic Market Gradually," located at <http://www.sda.gov.cn/WS01/CL0051/58315.html>, last visited on Apr. 11, 2014, 4 pages.
Undevia, S.D. et al. (Jun. 2005). "Pharmacokinetic Variability of Anticancer Agents," *Nature Reviews Cancer* 5(6):447-458.
Wikipedia (last modified Aug. 21, 2013). "Ischemia," located at http://en.wikipedia.org/wiki/Ischemia, last visited on Sep. 11, 2013, four pages.
Wikipedia (last modified on Sep. 8, 2013). "Paracetamol," located at http://en.wikipedia.org/wiki/Paracetamol, last visited on Sep. 11, 2013, 19 pages.
Written Opinion of the International Searching Authority mailed on Jul. 7, 2009, for PCT Patent Application No. PCT/US09/44746, filed on May 20, 2009, 5 pages.
Written Opinion of the International Searching Authority mailed on Jul. 16, 2009, for PCT Patent Application No. PCT/US09/44743, filed on May 20, 2009, 5 pages.
Written Opinion of the International Searching Authority mailed on Dec. 3, 2012, for PCT Patent Application No. PCT/US2012/056625, Internationally filed on Sep. 21, 2012, 5 pages.
U.S. Appl. No. 15/077,802, filed Mar. 22, 2016, for Muhammad et al.

\* cited by examiner

US 9,683,000 B2

CARBONATE PRODRUGS AND METHODS OF USING THE SAME

CROSS REFERENCE TO RELATED APPLICATIONS

This application is a Continuation of U.S. patent application Ser. No. 14/629,324, filed Feb. 23, 2015, which is a Continuation of U.S. patent application Ser. No. 14/252,683, now U.S. Pat. No. 8,993,545, issued on Mar. 31, 2015, which is a Divisional Patent Application of U.S. patent application Ser. No. 12/993,089, now U.S. Pat. No. 8,735,376, issued on May 27, 2014, which is a United States national phase application of PCT Application No. PCT/US2009/044746 having an International Filing Date of May 20, 2009, and claims priority benefit of U.S. Provisional Application No. 61/054,765, entitled "Carbonate Prodrugs and Methods of Using The Same", filed May 20, 2008, the contents of each of which are hereby incorporated by reference in their entirety as if they were set forth in full below.

BACKGROUND OF THE INVENTION

A drug which exhibits an excellent bioactivity and safety profile when tested in experimental models may be less active and/or more toxic when administered to human subjects. One possible reason for this disparity is that a molecule may be unable to reach target site(s) of action at therapeutic concentrations and/or accumulate at toxic levels in one or more tissues. Such pharmacokinetic differences between in vitro and in vivo models, and between test species and humans, may significantly limit the therapeutic utility of certain compounds, making drug development a challenge.

Physicochemical properties therapeutically effective dosage, and route of administration, can each influence the pharmacokinetic profile of a drug molecule. The therapeutically effective dosage is fixed for a particular drug. Nonetheless, a change in the route of administration may allow a reduced drug dosage if the new route offers higher bioavailability. For instance, given suitable physicochemical properties, a drug with poor oral bioavailability requiring a high dosage may be formulated for parenteral administration at a lower dosage due to its improved bioavailability. However, a different route of administration is generally possible only if physicochemical properties of a given drug molecule are suitable for the new dosage form. The physicochemical makeup of many existing drugs limits their use to oral administration, resulting in high dosages and poor pharmacokinetic profiles. Accordingly, efforts have been made to modify the physicochemical properties of existing drugs and/or their formulations.

A drug with poor solubility will often exhibit poor bioavailability—a situation which can either hinder the drug development or require administration of high dosages to attain therapeutically effective blood levels of the drug. Tricor® (fenofibrate), for example, was launched as a 300 mg capsule. Particle size reduction to a fine powder increased the solubility of the drug and allowed a dosage reduction down to 200 mg. Addition of a surfactant to the fine powder led to a formulation with a bioavailability similar to the 300 mg and 200 mg dosages using only a 160 mg dosage tablet. Another bioequivalent formulation containing nano-particles of the drug allowed for an effective 145 mg dosage. Thus, a significant decrease in the dosage of Tricor® (greater than 100%) was achieved by increasing its solubility which led to an increase in bioavailability. However, despite some examples of solubility improvements from particle size reduction, the intrinsic conditions of oral administration (e.g., limited aqueous media in the GI tract) may limit the solubility and bioavailability enhancements for certain drugs.

Another technique used to increase solubility is to make molecular complexes of insoluble/poorly soluble drugs with more soluble molecules such as cyclodextrins. Itraconazole (Sporanox®), voriconazole (Vfend®) and zisprasidone (Geodon®) are examples of successful applications of this technique. However, this application generally requires a large excess of cyclodextrin relative to the amount of drug being solubilized and may not impart the desired increase in solubility to the entire drug sample (for instance, a dosage of 10 mg itraconazole, 200 mg of voriconazole, or 20 mg of zisprasidone requires 400 mg, 3200 mg, or 294 mg of cyclodextrin, respectively).

While the importance of discovering new drugs cannot be overstated, the ability to improve the physicochemical properties of existing drugs has it bounties. Therefore, there is still a clear and unmet need for improved drugs, such as prodrugs of existing drugs.

The disclosures of all publications, patents, patent applications and other references referred to herein are hereby incorporated herein by reference in their entireties.

BRIEF SUMMARY OF THE INVENTION

The present invention relates to prodrugs and methods of their use in therapy. One aspect provides a prodrug comprising (a) a moiety of parent drug, wherein the parent drug comprises a hydroxyl group or a carboxyl group, or both, and (b) a prodrug moiety of the formula —C(O)O—P(O)(OH)$_2$ wherein the prodrug moiety is bound to the moiety of the parent drug at the hydroxyl group and/or the carboxyl group providing a carbonate moiety, or a pharmaceutically acceptable salt thereof or solvate of the foregoing. In some of these embodiments, the parent drug is not a $C_1$-$C_6$ alcohol (e.g., not methanol, ethanol, or phenol). In some embodiments, the parent drug is a compound selected from the parent drug compounds of group (I), (I), or (III), as described herein.

In some embodiments, the prodrug is of formula (IV):

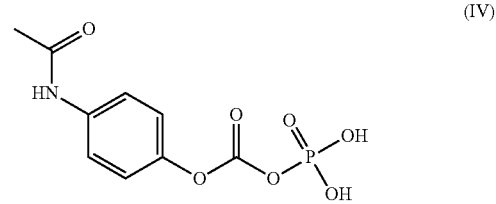 [SMILES: CC(=O)Nc1ccc(OC(=O)OP(=O)(O)O)cc1]

or a pharmaceutically acceptable salt thereof or solvate of the foregoing.

In some embodiments, the invention embraces a formulation comprising the prodrug of formula (IV) and a carrier. Also embraced are formulations comprising a carbonate prodrug as described herein of any one of the parent drugs selected from the group (I), (I), or (III) and a carrier. In some embodiments, the formulation comprises an effective amount of the prodrug and a carrier. In some embodiments, the carrier is a pharmaceutically acceptable carrier. In one aspect, the carrier is an aqueous carrier such as saline, which carrier may be at about physiological pH. In some embodiments, the invention embraces a substantially pure form of the prodrug.

In some embodiments, the invention embraces a formulation comprising the compound of formula (IV), or a pharmaceutically acceptable salt thereof or solvate of the foregoing, and an opioid, a non-steroidal anti-inflammatory drug (NSAID), a benzodiazepine and/or a barbiturate. In some embodiments, the invention embraces a formulation comprising the compound of formula (IV), or a pharmaceutically acceptable salt thereof or solvate of the foregoing, and codeine, morphine, hydrocodone, hydromorphone, levorphanol, aspirin, ketorolac, ibuprofen, naproxen, caffeine, tramadol, dextropropoxyphene, methylhexital, diazepam, lorazepam and/or midazolam.

In another aspect, the present invention provides methods of delaying the onset of parent drug action in an individual, comprising administering to the individual an effective amount the prodrug of formula (IV) or a carbonate prodrug as described herein of any one of the parent drugs selected from the group (I), (II), or (III), or a pharmaceutically acceptable salt thereof or solvate of the foregoing, wherein the prodrug provides a slower onset of parent drug action as compared to the parent drug.

In another aspect, the present invention provides methods of prolonging parent drug activity in an individual, comprising administering to the individual an effective amount of the prodrug formula (IV) or a carbonate prodrug as described herein of the parent drug selected from group (I), (II), or (III), or a pharmaceutically acceptable salt thereof or solvate of the foregoing, wherein the prodrug provides prolonged parent drug activity as compared to the parent drug.

In another aspect, methods of administering low volume/high concentration formulations are provided where the formulations comprise a carbonate prodrug of a parent drug and wherein the prodrug exhibits enhanced solubility (e.g., water solubility) as compared to the solubility of the parent drug. Low volume/high concentration formulations are also provided herein, such as formulations comprising a prodrug of the formula (IV) and a pharmaceutically acceptable carrier. A "low volume/high concentration" formulation intends a formulation comprising a carrier and a prodrug where a given volume of carrier contains a higher molar concentration of prodrug than is available or obtainable using the parent drug. Taking the prodrug of the formula (IV) as an example, a low volume/high concentration of such prodrug intends a formulation comprising a carrier and the prodrug wherein the formulation contains a higher molar concentration of prodrug in a given volume of carrier than is available or obtainable using acetaminophen. Methods of providing low volume/high concentrations of parent drug (e.g., acetaminophen) are also provided comprising administering to an individual a low volume/high concentration formulation of a prodrug as detailed herein (e.g., a prodrug of formula (IV) or a salt thereof or solvate of the foregoing). In one aspect, the methods entail administering a prodrug that results in rapid release of parent drug when administered to an individual (e.g., by enzymatic cleavage or hydrolysis). Also provided are methods of providing a single dose of parent drug in an amount that exceeds currently available doses by administering a prodrug as detailed herein.

In another aspect, the present invention provides methods of treating a disease or condition that is responsive to a parent drug, comprising administering to an individual an effective amount of the prodrug of formula (IV) or a carbonate prodrug as described herein of the parent drug selected from group (I), (II), or (III), or a pharmaceutically acceptable salt thereof or solvate of the foregoing.

In another aspect, the present invention provides methods of treating a disease or condition that is responsive to responsive to a parent drug, comprising administering to an individual a formulation comprising a prodrug of formula (IV) or a carbonate prodrug as described herein of the parent drug selected from group (I), (II), or (III), or a pharmaceutically acceptable salt thereof or solvate of the foregoing.

In some embodiments, the invention provides a method of treating a disease or condition that is responsive to acetaminophen, comprising administering to an individual an effective amount of the prodrug of formula (IV) or a pharmaceutically acceptable salt thereof or solvate of the foregoing. In some of these embodiments, the disease or condition is selected from the group consisting of pain, fever, inflammation, ischemic injury (e.g., myocardial and/or cerebral), and neuronal injury.

In some embodiments of the methods, the prodrug is administered parenterally (e.g., intravenously, intramuscularly, or subcutaneously). In some embodiments, the dosage of the prodrug is about 300 mg to about 2.6 g. In other embodiments, the dosage of the prodrug is about 1.3 g to about 1.9 g. In some of these embodiments, the volume of the dosage is about 1-25 mL. In other embodiments, the volume of the dosage is about 10-20 mL. In other embodiments, the volume of the dosage is about 1-10 mL. In other embodiments, the volume of the dosage is about 5-10 mL.

In another aspect is provided the use of a compound of prodrug of formula (IV) or a pharmaceutically acceptable salt thereof or solvate of the foregoing for the manufacture of a medicament for the treatment of a condition responsive to acetaminophen. In another aspect is provided the use of a compound of prodrug of formula (IV) or a pharmaceutically acceptable salt thereof or solvate of the foregoing for the treatment of a condition responsive to acetaminophen. In some variations, the condition is pain, fever, inflammation, ischemic injury, or neuronal injury.

In another aspect, the present invention provides kits for the treatment or prevention of a disease or condition responsive to a parent drug, comprising a prodrug of formula (IV) or a prodrug of the parent drug selected from group (I), (II), or (III), or a pharmaceutically acceptable salt thereof or solvate of the foregoing, and instructions for use.

In another aspect, the present invention provides kits for the treatment or prevention of pain, fever, inflammation, ischemic injury, or neuronal injury, comprising a prodrug of formula (IV) or a pharmaceutically acceptable salt thereof or solvate of the foregoing, and instructions for use.

DETAILED DESCRIPTION OF THE INVENTION

Figure 1:
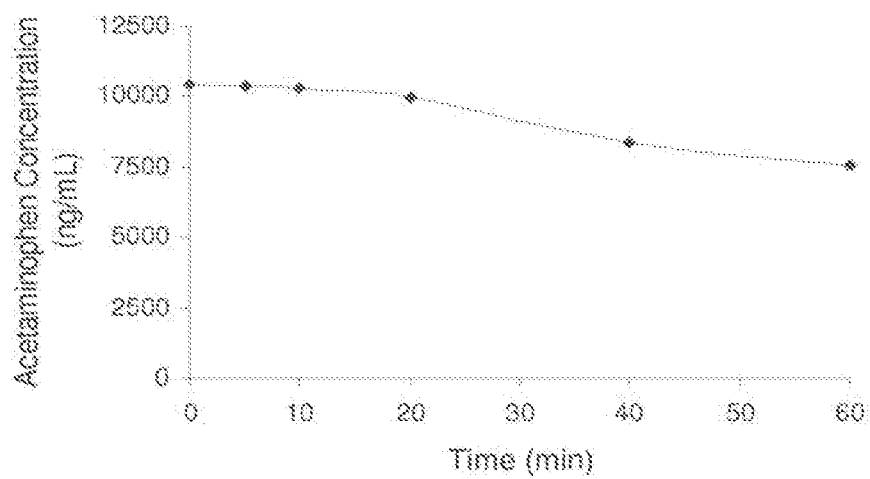
FIG. 1 shows data for the formation of acetaminophen from 15 μg/mL of the compound of formula (IV) in human plasma.

The present invention provides carbonate prodrugs which comprise a carbonic phosphoric anhydride prodrug moiety attached to the hydroxyl and/or carboxyl group of a parent drug moiety. It is understood that a suitable parent drug may contain either a hydroxyl or a carboxyl group or it may contain one or more of both a hydroxyl group and a carboxyl group. These prodrugs, upon hydrolysis, are believed to generate carbonic acid and inorganic phosphate, or inorganic phosphate alone, in addition to the released active parent drug. Carbonic acid is generally unstable and dissociates to form water and carbon dioxide. These byproducts, including the inorganic phosphate, are normally present in vivo and therefore are not expected to present unknown or undesirable effects.

The prodrugs of the present invention may provide increased solubility and/or improved safety profiles over administration of the parent drugs. In some instances, the prodrugs may be less susceptible to in vivo degradation and exhibit a greater half-life than its parent drug. A prodrug with a greater half-life is likely to require less frequent dosing and/or reduced dose than that of a parent drug, which can particularly be important when parent drug administration is accompanied by unfavorable side effects, such as nausea or when optimal dosing frequency promotes non-compliance. Further, a prodrug with different physicochemical characteristics than a parent drug may be more amenable to certain drug delivery routes, such as parenteral administration.

Accordingly, the present invention in one aspect provides a prodrug comprising the group —OC(O)O—P(O)(OH)$_2$.

In another aspect, the present invention provides methods of treating a disease or condition that is responsive to a parent drug, comprising administering to an individual an effective amount of a carbonate prodrug described herein.

Also provided are kits, formulations, and unit dosage forms of the carbonate prodrugs.

ABBREVIATIONS AND DEFINITIONS

Nomenclature of some compounds described herein may be identified using ChemDraw Ultra Version 10.0, available from CambridgeSoft®. Nomenclature of some drugs described herein may be identified from the USAN (United States Adaped Name), INN (International Nonproprietary Name) or JAN (Japanese Approved Name).

The term "prodrug" refers to a compound which provides an active compound following administration to the individual in which it is used, by a chemical and/or biological process in vivo (e.g., by hydrolysis and/or an enzymatic conversion). The prodrug itself may be active, or it may be relatively inactive, then transformed into a more active compound. The invention embraces prodrugs of parent drugs comprising a hydroxyl group and/or a carboxyl group, as described herein. The term "carbonate prodrug" refers to a prodrug comprising a carbonate moiety. —OC(O)O—. Non-limiting examples include prodrugs comprising the groups —OC(O)O—P(O)(OH)$_2$ and/or —C(O)O—C(O)O—P(O)(OH)$_2$ or salts thereof.

As used herein, "parent drug" refers to a drug that does not contain a prodrug moiety. A "parent drug moiety" or "moiety of parent drug" is a monovalent radical derived from a parent drug that may be attached to a "prodrug moiety" to provide the prodrug, as represented by the following schematic:

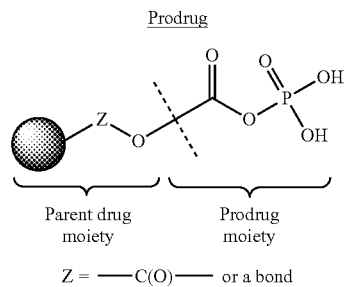

Z = —C(O)— or a bond

For example, acetaminophen is the parent drug to the prodrug (4-acetamidophenyl carbonic) phosphoric anhydride, wherein the prodrug comprises a parent drug moiety (the acetaminophen radical) and a prodrug moiety (—C(O)O—P(O)(OH)$_2$).

"Protecting group" refers to a chemical group that exhibits the following characteristics: 1) is stable to the projected reactions for which protection is desired; 2) is removable from the protected substrate to yield the desired functionality; and 3) is removable by reagents compatible with the other functional group(s) present or generated in such projected reactions. Selection of suitable protecting groups for use in the methods described herein is within the ordinary skill level in the art. Examples of suitable protecting groups can be found in Greene wt al. (2006) PROTECTIVE GROUPS IN ORGANIC SYNTHESIS, 4th Ed. (John Wiley & Sons, Inc., New York). A "hydroxy protecting group" as used herein denotes a group capable of protecting a free hydroxy group to generate a "protected hydroxyl" which, subsequent to the reaction for which protection is employed, may be removed without disturbing the remainder of the compound. Exemplary hydroxy protecting groups include, but are not limited to, ethers (e.g., allyl, triphenylmethyl (trityl or Tr), benzyl, p-methoxybenzyl (PMB), p-methoxyphenyl (PMP)), acetals (e.g., methoxymethyl (MOM), 3-methoxyethoxymethyl (MEM), tetrahydropyranyl (THP), ethoxy ethyl (EE), methylthiomethyl (MTM), 2-methoxy-2-propyl (MOP), 2-trimethylsilylethoxymethyl (SEM)), esters (e.g., benzoate (Bz), allyl carbonate, 2,2,2-trichloroethyl carbonate (Troc), 2-trimethylsilylethyl carbonate), silyl ethers (e.g., trimethylsilyl (TMS), triethylsilyl (TES), triisopropylsilyl (TIPS), triphenylsilyl (TPS), tert-butyldimethylsilyl (TBDMS), tert-butyldiphenylsilyl (TBDPS) and the like.

As used herein, "treatment", "treating", or "treat" is an approach for obtaining beneficial or desired results, including clinical results. For purposes of this invention, beneficial or desired results include, but are not limited to, one or more of the following: decreasing one or more symptoms of a disease or condition that is responsive to a parent drug, diminishing the extent of a disease or condition that is responsive to a parent drug, stabilizing a disease or condition that is responsive to a parent drug (e.g., preventing or delaying the worsening of a disease or condition responsive to a parent drug), delaying or slowing the progression of a disease or condition that is responsive to a parent drug, ameliorating a disease or condition that is responsive to a parent drug, decreasing the dose of one or more other medications required to treat the disease or condition that is responsive to a parent drug, and increasing the quality of life of an individual who has been or is suspected of having a disease or condition that is responsive to a parent drug. The disease or condition may be one that is or is believed to be responsive to a parent drug. The disease or condition may involve pain and the parent drug may be an analgesic. The disease or condition may be accompanied by inflammation. The disease or condition may be ischemic injury. The disease or condition may be a neuronal injury. In one variation, the condition is post-surgical pain and/or fever. In some embodiments, the carbonate prodrug and/or formulation comprising the prodrug reduces the severity of one or more symptoms associated with a disease or condition that is responsive to the parent drug by at least about any of 10%, 20%, 30%, 40%, 50%, 60%, 70%, 80%, 90%, 95%, or 100% compared to the corresponding symptom in the same subject prior to treatment or compared to the corresponding symptom in other subjects not receiving the prodrug and/or formulation. "Responsive to a parent drug" as used herein refers to a disease or condition, and/or symptom of a disease or condition which may be treated with the parent drug.

As used herein, "delaying" means to defer, hinder, slow, retard, stabilize, and/or postpone development of, and/or one or more symptoms of, a disease or condition that is responsive to a parent drug. This delay can be of varying lengths of time, depending on the history of the disease and/or individual being treated. As is evident to one skilled in the art, a sufficient or significant delay can, in effect, encompass prevention, in that the individual does not develop a disease or condition that is responsive to a parent drug. A method that "delays" development of disease or condition that is responsive to a parent drug is a method that reduces the probability of development of a disease or condition that is responsive to a parent drug in a given time frame and/or reduces the extent of a disease or condition that is responsive to a parent drug in a given time frame, when compared to not using the method. Such comparisons are typically based on clinical studies, using a statistically significant number of subjects.

As used herein, "delaying the onset" or "delayed onset" refers to the increased time to onset of action provided by a carbonate prodrug as compared to administration of the molar equivalent of the parent drug within the same time period through the same route of administration. For example, the delayed release of the parent acetaminophen from the (4-acetamidophenyl carbonic) phosphoric anhydride may result in delayed systemic exposure to acetaminophen as compared to administration of the molar equivalent of acetaminophen to an individual. Similar results may be obtained by other carbonate prodrugs of the invention.

As used herein, "prolonging activity" or "prolonged activity" refers to the sustained action provided by a carbonate prodrug by virtue of the time required to release or otherwise generate the parent drug from the carbonate prodrug. For example, administration of the prodrug (4-acetamidophenyl carbonic) phosphoric anhydride may result in sustained release of the parent acetaminophen as compared to administration of the molar equivalent of acetaminophen over the same time period through the same route of administration. "Sustained release" refers to release of the parent drug, such as acetaminophen, at a rate such that the blood concentration of the parent drug, such as acetaminophen or a metabolite thereof, in an individual is maintained at or within the therapeutic range (e.g., above the minimum effective analgesic concentration but below toxic levels) for an extended duration. The extended duration in this context intends any time greater than the time that the molar equivalent of corresponding parent drug, administered through the same route, results in a parent drug (or metabolite thereof) blood concentration within the therapeutic range.

As used herein, an "at risk" individual is an individual who is at risk of developing a disease or condition that is responsive to a parent drug. An individual "at risk" may or may not have a detectable disease or condition that is responsive to a parent drug, and may or may not have displayed symptoms associated with a detectable disease or condition that is responsive to a parent drug prior to the treatment methods described herein. "At risk" denotes that an individual has one or more so-called risk factors, which are measurable parameters that correlate with development of a disease or condition that is responsive to a parent drug. An individual having one or more of these risk factors has a higher probability of developing a disease or condition that is responsive to a parent drug than an individual without these risk factor(s).

As used herein, "pharmaceutically acceptable" refers to a material that is not biologically or otherwise undesirable, e.g., the material may be incorporated (e.g., at the time of manufacturing or administration) into a pharmaceutical composition administered to an individual without causing any significant undesirable biological effects or interacting in a deleterious manner with any of the other components of the composition in which it is contained. As used herein, the term "pharmaceutically acceptable carrier," refers to, for example, solvents, stabilizers, pH-modifiers, tonicity modifiers, adjuvants, binders, diluents, etc., known to the skilled artisan that are suitable for administration to an individual (e.g., a human). Combinations of two or more carriers are also contemplated in the present invention. The pharmaceutically acceptable carrier(s) and any additional components, as described herein, should be compatible for use in the intended route of administration (e.g., oral, parenteral) for a particular dosage form. Such suitability will be easily recognized by the skilled artisan, particularly in view of the teaching provided herein. Pharmaceutically acceptable carriers or excipients have preferably met the required standards of toxicological and manufacturing testing and/or are included on the Inactive Ingredient Guide prepared by the U.S. Food and Drug administration.

The term, "effective amount," as used herein refers to an amount that results in a desired pharmacological and/or physiological effect in an individual who has or is suspected of having (e.g., based on symptoms and/or an individual's perceptions/feelings) a disease or condition responsive to a parent drug or who displays one or more of its symptoms. An effective amount may completely or partially prevent the occurrence or recurrence of the disease or condition responsive to a parent drug or symptom thereof and/or may be therapeutic in terms of a partial or complete cure for the disease or condition responsive to a parent drug and/or adverse effect attributable to the disease or condition (e.g., pain). In reference to a disease or condition described herein (e.g., pain), an effective amount may comprise an amount sufficient to, among other things, reduce and/or relieve to some extent one or more of the symptoms associated with a disease or condition that is responsive to a parent drug. In certain embodiments, the effective amount is sufficient to prevent the condition, as in being administered to an individual prophylactically. Effective amount includes the eradication or amelioration of the underlying condition being treated and/or eradication or amelioration of one or more of the symptoms associated with the underlying condition such that the individual reports an improvement in feeling or condition (e.g., decreased pain intensity and/or duration), notwithstanding that the individual may still be afflicted with the underlying disease or condition. Effective amount also includes halting or slowing the progression of the disease or condition, regardless of whether improvement or the disease or condition is realized.

The "effective amount" may vary depending on the composition being administered, the condition being treated/prevented (e.g., the type of pain), the severity of the condition being treated or prevented, the age, body size, weight, and relative health of the individual, the route and form of administration, the judgment of the attending medical or veterinary practitioner (if applicable), and other factors appreciated by the skilled artisan in view of the teaching provided herein. An effective amount may be assessed, for example, by using data from one or more clinical, physiological, biochemical, histological, electrophysiological, and/or behavioral evaluations.

As is understood in the art, an "effective amount" may be in one or more doses, i.e., a single dose or multiple doses may be required to achieve the desired treatment endpoint. An effective amount may be considered in the context of administering one or more additional pharmaceutical agents, and a carbonate prodrug may be considered to be given in an effective amount if, in conjunction with one or more additional pharmaceutical agents, one or more desirable or beneficial result(s) may be or are achieved.

When used with respect to methods of treatment and/or prevention and the use of the carbonate prodrugs thereof described herein, an individual "in need thereof" may be an individual who has been diagnosed with, previously treated for, and/or suspected of having the disease or condition to be treated. With respect to prevention, the individual in need thereof may also be an individual who is at risk for a disease or condition (e.g., a family history of the condition, life-style factors indicative of risk for the condition, etc.).

In some variations, the individual has been identified as having one or more diseases or conditions, and/or symptoms thereof described herein. Identification of the diseases or conditions and/or symptoms thereof by a skilled physician is routine in the art (e.g., detection of allergies, cold, cough, flu, pain, etc.) and may also be suspected by the individual or others, for example, due to pain, fever, etc.

In some embodiments, the individual has been identified as susceptible to one or more of the diseases or conditions as described herein. The susceptibility of an individual may be based on any one or more of a number of risk factors and/or diagnostic approaches appreciated by the skilled artisan, including, but not limited to, genetic profiling, family history, medical history (e.g., appearance of related conditions), lifestyle or habits.

In some embodiments, the individual is a mammal, including, but not limited to, bovine, horse, feline, rabbit, canine, rodent, or primate. In some embodiments, the mammal is a primate. In some embodiments, the primate is a human. In some embodiments, the individual is human, including adults, children, infants, and preemies. In some embodiments, the individual is a non-mammal. In some variations, the primate is a non-human primate such as chimpanzees and other apes and monkey species. In some embodiments, the mammal is a farm animal such as cattle, horses, sheep, goats, and swine; pets such as rabbits, dogs, and cats; laboratory animals including rodents, such as rats, mice, and guinea pigs; and the like. In some embodiments, the individual is a non-mammal, including, but not limited to, birds, and the like. The term "individual" does not denote a particular age or sex.

As used herein, "combination therapy" means a first therapy that includes a carbonate prodrug in conjunction with a second therapy (e.g., surgery and/or an additional pharmaceutical agent) useful for treating, stabilizing, preventing, and/or delaying the disease or condition. Administration in "conjunction with" another compound includes administration in the same or different composition(s), either sequentially, simultaneously, or continuously, through the same or different routes. In one variation, the combination therapy may include a carbonate prodrug and its corresponding parent drug. In some embodiments, the combination therapy optionally includes one or more pharmaceutically acceptable carriers or excipients, non-pharmaceutically active compounds, and/or inert substances.

As used herein, the term "additional pharmaceutical agent," refers to an active agent other than the carbonate prodrug (e.g., another drug and/or the parent drug itself) which is administered to elicit a therapeutic effect. The additional pharmaceutical agent(s) may be directed to (1) a therapeutic effect related to the disease or condition that the carbonate prodrug is intended to treat or prevent (e.g., pain), (2) treat or prevent a symptom of the underlying condition, (3) reduce the appearance or severity of side effects of administering the carbonate prodrug, and/or (4) a therapeutic effect related to a disease or condition that is not responsive to the parent drug or is relatively less responsive to the parent drug.

Reference to "about" a value or parameter herein includes (and describes) variations that are directed to that value or parameter per se. For example, a description referring to "about X" includes the description of "X".

As used herein and in the appended claims, the singular forms "a," "or," and "the" include plural referents unless the context clearly dictates otherwise. It is understood that aspect and variations of the invention described herein include "consisting" and/or "consisting essentially of" aspects and variations.

Unless defined otherwise or clearly indicated by context, all technical and scientific terms and abbreviations used herein have the same meaning as commonly understood by one of ordinary skill in the art to which this invention belongs.

Carbonate Prodrugs

The invention embraces prodrugs of corresponding parent drugs which may provide improved or altered physicochemical properties. Parent drugs may be modified in accordance with the invention to provide prodrugs that include a carbonate as described herein. A prodrug contains a parent drug moiety and a prodrug moiety where the prodrug moiety may be removable in vivo to provide parent drug moieties, or pharmaceutically acceptable salts thereof. The administration of the prodrug may result in one or more of: (1) capability of obtaining a higher blood level concentration of parent drug or metabolite thereof (e.g., due to increased solubility), (2) delayed onset of parent drug activity, (3) prolonged parent drug activity and/or (4) a similar blood level concentration when administered at a lower dosage as compared, on an parent drug molar equivalent basis, to administration of the parent drug itself.

In some embodiments, the carbonate prodrug comprises: (1) a parent drug moiety comprising a hydroxyl group and/or a carboxyl group; and (2) a prodrug moiety of the formula $-C(O)O-P(O)(OH)_2$, wherein the prodrug moiety is linked to the parent drug moiety at the hydroxyl group and/or the carboxyl group to form a carbonate. In some embodiments, the parent drug comprises a carboxyl group and the prodrug moiety is linked to the parent drug moiety at the carboxyl group. In some embodiments, the parent drug comprises a hydroxyl group and the prodrug moiety is linked to the parent drug moiety at the hydroxyl group. In some of these embodiments, the parent drug moiety is other than a $C_1$-$C_6$ alcohol. In one of these embodiments, the parent drug moiety is other than methanol, ethanol, or phenol.

In some embodiments, the invention embraces prodrugs comprising the moiety —OC(O)O—P(O)(OH)$_2$. In some of these embodiments, the prodrug is other than CH$_3$—OC(O)O—P(O)(OH)$_2$, CH$_3$CH$_2$—OC(O)O—P(O)(OH)$_2$, or Ph-OC(O)O—P(O)(OH)$_2$. In some embodiments, the invention embraces prodrugs comprising the moiety —C(O)O—C(O)O—P(O)(OH)$_2$.

In some embodiments, the prodrug comprises only one prodrug moiety. In some embodiments, the prodrug comprises only two prodrug moieties. In some embodiments, the prodrug comprises two or more prodrug moieties. In some embodiments, the parent drug moiety is of a parent drug comprising only one hydroxyl group and no carboxyl groups. In some embodiments, the parent drug moiety is of a parent drug comprising only one carboxyl group and no hydroxyl groups. In some embodiments, the parent drug moiety is of a parent drug comprising two or more hydroxyl groups. In some embodiments, the parent drug moiety is of a parent drug comprising two or more carboxyl groups. In some embodiments, the parent drug moiety is of a parent drug comprising only one carboxyl group and only one hydroxyl group.

The invention embraces the use of any parent drug with a hydroxyl group and/or a carboxyl group. Examples of parent drugs comprising a hydroxyl group include, without limitation compounds of group (I): acetaminophen, hydroquinone, metacresol, resorcinol, parachlorophenol, guaiacol, phloroglucinol, chlorocresol, mequinol, mercufenol (e.g., mercufenol chloride), salicylamide, chloroxylenol, vanillin, chlorzoxazone, thymol, methylparaben, phenolsulfonic acid, paroxypropione, resorcinol, brocresine, chlorindanol, oxyquinoline, norepinephrine, octopamine, dopamine, vanillin, norfenefrine, ethylparaben, cloxyquin, eugenol, hydroxyamphetamine, oxidopamine, tetroquinone, epinephrine, hyrnecrornone, phenylephrine, propofol, iodoquinol, edrophonium (e.g., edrophonium chloride), flopropione, propylparaben, glycol salicylate, levonordefrin, mephenesin, adrenalone, chloroxine, clioquinol, halquinols, melizame, racepinephrine, aminosalicylate, epinephrine, guaifenesin, butylparaben, etilefrine, hexylresorcinol, racepinephrine, roxarsone, propyl gallate, clorophene, deterenol, epinephryl borate, monobenzone, warfarin, seclazone, chlorphenesin carbamate, methoxamine, bucetin, isoproterenol, isoprenaline, butylated hydroxytoluene, ethamivan, etilevodopa, naproxol, tapentadol, anthralin, methocarbamol, carbidopa, osalmid, albuterol, berefrine, drometrizole, fadolrnidine, fenticlor, isoetharine, oxybenzone, phenyl aminosalicylate, prenalterol, profadol, stiripentol, triclosan, pindolol, eptazocine, isoetharine, levalbuterol, benserazide, dibromsalan, dioxybenzone, enofelast, fosalan, idronoxil, metabromsalan, methyldopa, octisalate, rimiterol, atenolol, bithionol, dezocine, alprenolol, midodrine, bunitrolol, bupranolol, esatenolol, benserazide, metoprolol, nitecapone, ciclafrine, ciramadol, homosalate, nonoxynol 4, panadol, quindonium, nonoxynol 9, propranolol, diethylstilbestrol, tolcapone, dienestrol, oxymetazoline, tramadol, hexestrol, oxprenolol, bensalan, butoxamine, axomadol, carbuterol, ciramadol, cyclazocine, dexpropanolol, soterenol, prinaberel, niclosamide, pentazocine, venlafaxine, hexachlorophene, ritodrine, colterol, dextrorphan, embutranlide, fengabine, isomolpan, ketazocine, moxazocine, naxagolide, phenprocoumon, sulfonterol, sulisobenzone, cianidanol, capsaicin, nadolol, esmolol, entacapone, metaraminol, benzbromarone, ritodrine, befunolol, benziodarone, metipranolol, procaterol, alentemol, bumetrizole, bunolol, butopamine, dobutamine, equilin, exaprolol, fenoterol, fluorosalan, galantamine, isoetharine, levalbuterol, masoprocol, pranolium chloride, prifelone, proxicromil, raclopride C11, rotigotine, tazofelone, tebufelone, zucapsaicin, estrone, estradiol, betaxolol, hydromorphone, oxymorphone, fenoterol, nylidrin, nipradilol, isoxsuprine, metipranolol, epinephrine, bisoprolol, denopamine, tomelukast, anthramycin, dopamantine, levobetaxolol, lomofungin, norepinephrine, oxilorphan, progabide, ractopamine, taleranol, xipamide, zeranol, estriol, codeine, octabenzone, oxycodone, oxyfedrine, bufetolol, oxymetebanol, drotebanol, idebenone, acebutolol, primidolol, befloxatone, arbutamine, biphenamine, butorphanol, cicloprolol, kalafungin, ketorfanol, octrizole, phenolphthalein, tolgabide, xamoterol, dronabinol, ethinylestradiol, acebutolol, labetalol, magnesium salicylate, bergenin, phenolsulfonphthalein, fluorescein, naloxone, dilevalol, dipivefrin, amodiaquine, dicumarol, ecopipam, epimestrol, nalmefene, naltrexone, oxyphenbutazone, salethamide, tipropidil, atovaquone, phentolamine, mestranol, fenoldopam, dipivefrin, siccanin, bevantolol, meluadrine, trimetoquinol (tretoquinol), naltrexone, nalmefene, morphine, buquinolate, cyproquinate, dopexamine, estradiol, estrazinol, tinabinol, nalbuphine, amosulalol, pentazocine, ethylmorphine, cefadroxil, oxyquinoline, optochin, amoxicillin, guaithylline, medroxalol, menoctone, modecainide, nalmexone, pentamorphone, rafoxanide, sulfinalol, tepoxalin, tidembersat, tipentosin, zinterol, methylnaltrexone, epanolol, toborinone, dihydrocodeine, desvenlafaxine, bucindolol, ciladopa, darbufelone, prinomastat, dopexamine, medroxalol, mesuprine, salantel, estradiol, enprostil, naftopidil, quinine, acrisorcin, alvocidib, droloxifene, fenprostalene, fenretinide, incyclinide, nabilone, nebivolol, reproterol, sabeluzole, afirnoxifene, osutidine, beraprost, ezetimibe, tocopherol, pinoxepin, ciprefadol, closantel, decoquinate, lubeluzole, salmeterol, estradiol, ledoxantrone, meralein sodium, nylestriol, paliperidone, ranolazine, tonazocine, xorphanol, zenazocine, sedoxantrone, levorphanol, levallorphan, sulprostone, cetocycline, estramustine, piroxantrone, sancycline, sarmoxicillin, sibenadet, tebuquine, traxoprodil, nebivolol, sergliflozin, suplatast, axitirome, dasantafil, demecycline, dihydrocodeine, enciprazine, quadazocine, ranolazine, teloxantrone, trimazosin, tetracycline, butorphanol, tolterodine, mitoxantrone, bendacalol, bialamicol, demeclocycline, methacycline, nisbuterol, doxycycline, metaproterenol, methacycline, barnethan, travoprost, silodosin, raloxifene, hexoprenaline, acolbifene, arformoterol, arzoxifene, epitetracycline, minocycline, nantradol, nitrocycline, oxytetracycline, chlortetracycline, puromycin, Nalfurafine, terbutaline, Idarubicin, clomocycline, Indenolol, sulfobromophthalein, carubicin, quinidine, salbutamol, bitolterol, daunorubicin, moxalactam, latamoxef, adaprolol, bazedoxifene, bosentan, rolitetracycline, lurtotecan, menogaril, lasofoxifene, quinterenol, steffimycin, tocophersolan, droloxifene, zosuquidar, hesperidin, salmeterol, tigecycline, fulvestrant, atovaquone, edotecarin, levalbuterol, oxantel, novobiocin, apomorphine, procaterol, etoposide, rutin, metoprolol, lopinavir, rescimetol, bemotrizinol, levo-dobutamine, metkephamid, penbutolol, nelfinavir, irinotecan, gamma oryzanol, enalkiren, elsamitrucin, neocarzinostatin, zorubicin, liotrix, meclocycline, esculin, rifamycin, teniposide, maytansine, valrubicin, pamatolol, temoporfin, tubocurarine, hydroxyzine, trabectedin, proxorphan, xamoterol, rifamexil, rifaximin, nogalamycin, vindesine, formoterol, ifenprodil, rifamide, aclarubicin, rifampicin, quinidine, bizelesin, rifametane, lavoltidine, seglitide, rifapentine, vinblastine, vincristine, rifalazil, oxytocin, aspartocin, ovemotide, diphenidol, perphenazine, and vapreotide.

Examples of parent drugs comprising a carboxyl group include, without limitation, compounds of group (II): aspirin, naproxen, gemfibrozil, ciprofibrate, ethacrynic acid, cinoxacin, pranoprofen, fenclofenac, miloxacin, oxolinic acid, ticrynafen, ticrynafen, droxacin (e.g., droxacin sodium), flufenisal, furaprofen, furobufen, isoxepac, anirolac, benoxaprofen, furegrelate, salcaprozate, tixanox, protizinic acid, febuxostat, trepibutone, brocrinat, pazufloxacin, cetraxate, capobenic acid, nafenopin, sulotroban, xanoxate, tranilast, tolrestat, acitretin, indacrinone, iopronic acid, mycophenolate, thyroxine I-125, thyroxine I-131, indomethacin, bumetanide, piretanide, cilomilast, mofezolac, efaproxiral, lifibrol, tifurac, cefadroxil, ofloxacin, olopatadine, levothyroxine, efaproxiral, minocromil, oxarbazole, probicromil, phenethicillin, fluorescein, nedocromil, zidometacin, veliflapon, tesaglitazar, propicillin, codoxime, levopropylcillin, acemetacin, methicillin, beraprost, varespladib, moxifloxacin, balofloxacin, balsalazide, sivelestat, premafloxacin, grepafloxacin, adapalene, elvitegravir, tirofiban, sarpogrelate, tiplasinin, methyldopa, repaglinide, Sofalcone, sodelglitazar, clinofibrate, carfecillin (carbenicillin phenyl), ticarcillin cresyl, sivelestat, trimebutine, ablukast, ertiprotafib, moexipril, firategrast, candoxatril, carbenicillin indanyl, garenoxacin, polifeprosan 20, atrasentan, muraglitazar, fenoprofen, peliglitazar, farglitazar, elsibucol, quiflapon, succinobucol, lapaquistat, ecopladib, levofloxacin, and gatifloxacin.

Examples of parent drugs comprising both a hydroxyl group and a carboxyl group include, without limitation, compounds of group (III): salicylic acid, aminosalicylic acid, mesalazine (mesalamine), oxfenicine, tyrosine, levodopa, metyrosine, bismuth subgallate, iotyrosine I-131, droxidopa, diotyrosine I-125, fluorodopa F-18, diflunisal, salsalate, salnacedin, pirenoxine, liothyronine I-125, liothyronine I-131, mycophenolic acid, olsalazine (e.g., olsalazine sodium), talibegron, cefadroxil, amoxicillin, sulfasalazine, deferasirox, cefprozil, fendosal, beraprost, bentiromide, cloprostenol, treprostinil, carbidopa, sermetacin, merbromin, cefatrizine, fumoxicillin, alvimopan, cefaparole, lamifiban, rose bengal, cromoglycate, propylene glycolate, streptonigrin, tipelukast, fidexaban, moxalactam, doxorubicin, esorubicin, epirubicin, etalocib, eltrombopag, cefpiramide, benzoylpas, lasalocid, aplaviroc, pirarubicin, lymecycline, cefoperazone, cloperastine, thymopentin, piridicillin, sennosides, bimosiamose, and pivampicillin.

In some embodiments, the parent drug moiety is any parent drug shown in group (III) comprising only one prodrug moiety, wherein the prodrug moiety is liked through a carboxyl group. In some embodiments, the parent drug moiety is any parent drug shown in group (III) comprising only one prodrug moiety, wherein the prodrug moiety is liked through a hydroxyl group. In some embodiments, the parent drug moiety is any parent drug shown in group (III) comprising two or more prodrug moieties, wherein at least one the prodrug moiety is liked through a carboxyl group and at least one the prodrug moiety is liked through a hydroxyl group.

In some embodiments, the prodrug is of formula (IV):

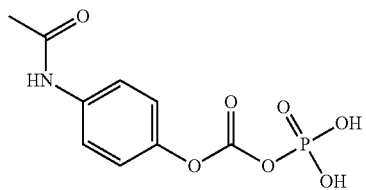 [SMILES: CC(=O)Nc1ccc(OC(=O)OP(=O)(O)O)cc1]

(IV): (4-acetamidophenyl carbonic) phosphoric anhydride. Pharmaceutically acceptable salts of the prodrug of formula (IV) are also provided.

In some embodiments, the carbonate prodrugs of the invention have increased solubility (e.g., increased water solubility) relative to their parent drug moieties. For example, (4-acetamidophenyl carbonic) phosphoric anhydride has a water solubility at room temperature of more than 10 times that of acetaminophen (152 mg/mL and about 15 mg/mL, respectively) (See Tu Lee et. al. *Pharmaceutical Technology*, Oct. 2, 2006). Increased water solubility may render the prodrugs more suitable for parenteral administration and may also permit a higher blood level concentration, if desired, of the parent drug or a metabolite thereof and/or allow a lower dosage to obtain a similar blood level concentration when compared to the parent drug moieties on a molar equivalent basis. In some embodiments, the prodrugs are greater than 2, 3, 5, 10, 15, 25, 50, 100, 200, 500 or 1000 times more soluble in water than their parent drug moieties under the same conditions.

The prodrugs described herein may be relatively stable under some conditions (e.g., during storage and/or preparation in a saline solution), while being converted to their parent drugs under other conditions (e.g., following introduction into an in vitro or in vivo system, such as administration into an individual). In some embodiments, the prodrug (e.g., the acetaminophen prodrug of formula IV at, for example, about 0.3 ng/mL or about 15 ng/mL, or between about 0.3 ng/mL and about 15 ng/mL, in plasma) is capable of greater than 10%, or 15%, or 20%, or 25%, or 30%, or 35%, or 40%, or 45%, or 50%, or 60%, or 75% conversion to the parent drug (e.g., acetaminophen) after about any of 1 min, 5 min, 10 min, 15 min, 20 min, 30 min, 45 min. or 1 hr at 37° C. In some embodiments, the prodrug (e.g., the acetaminophen prodrug of formula IV at, for example, about 0.3 ng/mL or about 15 ng/mL, or between about 0.3 ng/mL and about 15 ng/mL in human plasma) is capable of greater than about 50%, or about 60% conversion to the parent drug (e.g., acetaminophen) after about 1 min, or about 5 min at 37° C. In some of these embodiments, the prodrug (e.g., acetaminophen prodrug of formula IV) is not capable of said conversion to the parent drug (e.g., acetaminophen) in water, propylene glycol and/or saline at room temperature. For example, in some of these embodiments, the prodrug is not capable of more than any of about 5%, or 10%, or 20%, or 25%, or 30% or 40%, or 60%, or 70% conversion to parent drug at 30 min or 60 min in water or propylene glycol at room temperature. In one embodiment, the acetaminophen prodrug of formula IV at a concentration of about 15 ng/mL (or about 0.3 ng/mL, or between about 0.3 ng/mL and about 15 ng/mL) in human plasma at 37° C. is capable of greater than 50% conversion to the parent drug after 5 min, and is not capable at the same concentration in water at room temperature of more than 30% conversion at 30 min. In some embodiments, the prodrug (e.g., the acetaminophen prodrug of formula IV) is capable of at least 10%, 20%, 30%, 40%, 50%, 60%, 70%, 80%, or 90% increased conversion to parent drug in human plasma at 37° C. compared to water at room temperature after the same time of exposure.

In some embodiments, the carbonate prodrug is in substantially pure form. Unless otherwise stated, "substantially pure" intends a preparation of the prodrug that contains no more than 15% impurity, wherein the impurity intends compounds other than the carbonate prodrug, but does not include the parent drug or other forms or the prodrug (e.g., different salt or non-salt versions of the prodrug). In one variation, a preparation of substantially pure prodrug is provided wherein the preparation contains no more than 50% impurity. In one another variation, a preparation of substantially pure prodrug is provided wherein the preparation contains no more than 25% impurity, or no more than 10% impurity, or no more than 5% impurity, or no more than 3% impurity, or no more than 1% impurity, or no more than 0.5% impurity.

The invention also embraces all of the solvate, hydrate and/or salt (e.g., pharmaceutically acceptable salt) forms of the carbonate prodrug described herein and methods of using the same. In some embodiments, the carbonate prodrug of the present invention can exist in unsolvated forms as well as solvated forms (i.e., solvates). The prodrugs may also include hydrated forms (i.e., hydrates).

The invention embraces all salts of the carbonate prodrug (e.g., the prodrug of formula (IV)) described herein, as well as methods of using such salts of the prodrugs. The invention also embraces all non-salt forms of any salt of a prodrug described herein, as well as other salts of any salt of a prodrug named herein. In some embodiments, the salts of the prodrugs are pharmaceutically acceptable salts. "Pharmaceutically acceptable salts" are those salts which retain the biological activity of the free prodrugs and which can be administered as drugs or pharmaceuticals to an individual (e.g., a human). In some embodiments, the carbonate prodrugs are mono- or di-substituted by alkali metal or alkaline earth metals. In some embodiments, the carbonate prodrug is a mono alkaline phosphate salt (e.g., mono sodium phosphate salt). In some embodiments, the carbonate prodrug is a di-alkaline phosphate salt (e.g., disodium phosphate salt). The desired salt of a basic functional group of a compound may be prepared by methods known to those of skill in the art by treating the compound with an acid. The desired salt of an acidic functional group of a compound can be prepared by methods known to those of skill in the art by treating the compound with a base. Examples of inorganic salts of acid compounds include, but are not limited to, alkali metal and alkaline earth salts, such as sodium salts, potassium salts, magnesium salts, bismuth salts, and calcium salts; ammonium salts; and aluminum salts. Examples of organic salts of acid compounds include, but are not limited to, procaine, dibenzylamine, N-ethylpiperidine, N,N'-dibenzylethylenediamine, trimethylamine, and triethylamine salts.

Synthetic Methods

The compounds of the invention may be prepared using a number of methods familiar to one of skill in the art. The discussion below is offered to illustrate certain methods available for use in assembling the carbonate prodrugs and is not intended to limit the scope of the reactions or reaction sequences and/or conditions that are useful in preparing the prodrugs.

Some target compounds of the invention may be synthesized by starting with a parent drug moiety containing a hydroxyl and/or carboxyl group as shown below in Scheme I. Treatment with phosgene under basic conditions (e.g., N,N-diethyl aniline) can be used to generate the carbonochloridate or carbonochloridic anhydride (where Z is a bond or —C(O)—, respectively). Further treatment with a protected phosphate (e.g., di-tert-butyl hydrogen phosphate) with base (e.g., triethylamine) yields the protected phosphoric anhydride, which can be deprotected under a variety of conditions, for example using acid (e.g., acetic acid).

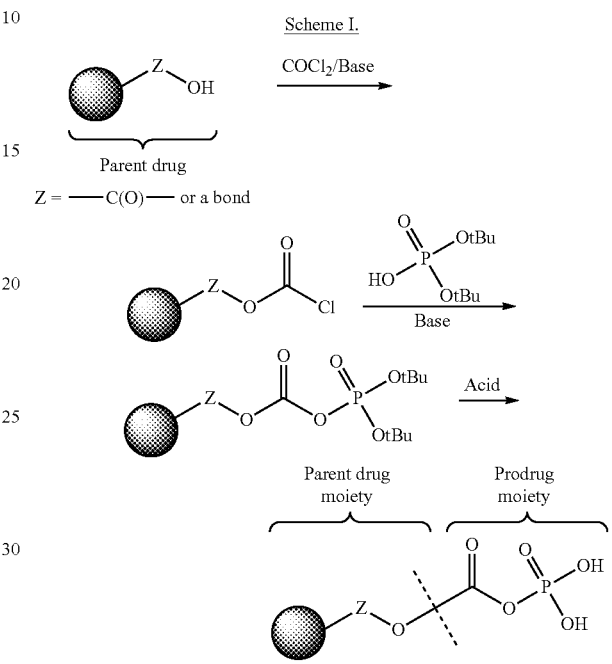

The invention also embraces methods of preparing the prodrugs described herein. In one aspect is provided a process for preparing a compound of formula (V):

(V)

Parent drug moiety    Prodrug moiety wherein Z is —C(O)— or a bond; or a pharmaceutically acceptable salt thereof or solvate of the foregoing; comprising
(a) reacting a compound of formula SV-A:

(SV-A)

or a pharmaceutically acceptable salt thereof or solvate of the foregoing, with phosgene;
(b) reacting the compound formed from step (a), or a pharmaceutically acceptable salt thereof or solvate of the foregoing, with a di-protected phosphate in a suitable solvent; and (c) deprotection of the di-protected phosphate of the compound formed from step (b).

In some embodiments of step (a) for the process for preparing a compound of formula V, the reaction further comprises base. In some embodiments of step (a), the reaction further comprises N,N-diethyl aniline or triethylamine. In some embodiments of step (b) for the process for preparing a compound of formula I, the di-protected phosphate is di-tert-butyl phosphate or dibenzylphosphate. In some embodiments of step (b), the suitable solvent is a chlorinated solvent (e.g., chloroform). In some embodiments of step (b), the reaction further comprises N,N-diethyl aniline or triethylamine. In some embodiments of step (c) for the process for preparing a compound of formula V, the deprotection comprises reducing conditions. In some embodiments of step (c), the deprotection comprises using $Pd(OH)_2/H_2$. In some embodiments of step (c), the deprotection comprises acidic conditions. In some embodiments of step (c), the deprotection comprises treatment with acetic acid. In some embodiments of step (c), the suitable solvent is a protic solvent (e.g., methanol). In some of these embodiments, the compound of formula V is (4-acetamidophenyl carbonic) phosphoric anhydride.

Formulations

The carbonate prodrugs described herein can be in formulations (including pharmaceutical compositions) with additives such as excipients (e.g., one or more excipients), antioxidants (e.g., one or more antioxidants), stabilizers (e.g., one or more stabilizers), preservatives (e.g., one or more preservatives), pH adjusting and buffering agents (e.g., one or more pH adjusting and/or buffering agents), tonicity adjusting agents (e.g., one or more tonicity adjusting agents), thickening agents (e.g., one or more thickening agents), suspending agents (e.g., one or more suspending agents), binding agents (e.g., one or more binding agents, viscosity-increasing agents (e.g., one or more viscosity-increasing agents), and the like, either alone or together with one or more additional pharmaceutical agents, provided that the additional components are pharmaceutically acceptable for the particular disease or condition to be treated. In some embodiments, the formulation may include combinations of two or more of the additional components as described herein (e.g., 2, 3, 4, 5, 6, 7, 8, or more additional components). In some embodiments, the additives include processing agents and drug delivery modifiers and enhancers, such as, for example, calcium phosphate, magnesium stearate, talc, monosaccharides, disaccharides, starch, gelatin, cellulose, methyl cellulose, sodium carboxymethyl cellulose, dextrose, hydroxypropyl-β-cyclodextrin, polyvinylpyrrolidinone, low melting waxes, ion exchange resins, and the like, as well as combinations of any two or more thereof. Other suitable pharmaceutically acceptable excipients are described in REMINGTON'S PHARMACEUTICAL SCIENCES, Marck Pub. Co., New Jersey 18$^{th}$ edition (1996), and REMINGTON: THE SCIENCE AND PRACTICE OF PHARMACY, Lippincott Williams & Wilkins, Philadelphia, 20$^{th}$ edition (2003) and 21$^{st}$ edition (2005).

The formulations may vary or be tailored according to the condition to be treated, the amount of compound to be administered, the condition of the individual, and other variables that will readily be apparent to one of ordinary skill in the art in view of the teachings provided herein.

In some embodiments, the formulation (e.g., formulations amenable to parenteral administration) is an aqueous formulation with a pH from about 3.5 to about 9.5, or from about 4.5 to about 8.5, or from about 5.0 to about 9.0, or from about 5.5 to about 8.5, or from about 6.0 to about 8.0, or from about 6.5 to about 8.0, or from about 7.0 to about 8.0, or about 7.4.

Formulations comprising a carbonate prodrug described herein (e.g., acetaminophen prodrug of formula IV) and saline are provided. In one aspect, such formulations are at physiological pH (about 7.4). Such formulations may be amenable to storage and subsequent use with the prodrug remaining intact for prolonged periods of time (e.g., during storage) and converted to acetaminophen after administration to an individual (e.g., an adult, child, or infant). In some embodiments, the prodrug is stored as a dry powder and the formulation is generated by dissolving the dry powder in saline prior to administration. In one aspect, formulations are provided, e.g., formulations comprising the prodrug at a molar equivalent of about any of 50 mg/mL, 75 mg/mL, 100 mg/mL, 125 mg/mL, 150 mg/mL, 175 mg/mL, or 200 mg/mL of parent drug (e.g., acetaminophen), wherein the molar equivalent of prodrug is the amount of prodrug that would result in the indicated amount of parent drug upon complete conversion. For any amount (e.g., dosage) of carbonate prodrug described herein, also contemplated is the molar equivalent of prodrug for that amount of parent drug. Single bolus formulations are also provided, e.g., up to about any of 5 mL, 10 mL, or 15 mL (at, for example, the stoichiometric prodrug equivalent of about 1450 mg to about 1600 mg of parent drug, such as acetaminophen).

Kits

The invention also provides kits containing materials useful for the treatment or prevention of a condition that is responsive to the parent drug (e.g., pain and/or fever). The kits may contain a carbonate prodrug of the invention (e.g., a prodrug of formula (IV) or a carbonate prodrug as described herein of any one of the parent drugs selected from the group (I), (II), or (III)) and instructions for use. The kits may comprise a container with a label. Suitable containers include, for example, bottles, vials, and test tubes. The containers may be formed from a variety of materials such as glass or plastic. The containers may hold a carbonate prodrug or a formulation of a carbonate prodrug (e.g., a formulation further comprising one or more additional pharmaceutical agents). The label on the container may indicate that the carbonate prodrug or the formulation is used for treating or suppressing a condition that is responsive to the parent drug (e.g., pain and/or fever), and may also indicate directions for either in vivo or in vitro use, such as those described herein.

The invention also provides kits comprising one or more of the carbonate prodrugs described herein (e.g., a prodrug of formula (IV) or a carbonate prodrug as described herein of any one of the parent drugs selected from the group (I), (II), or (III)). In some embodiments, the kit of the invention comprises the container described above. In other embodiments, the kit of the invention comprises the container described above and a second container comprising a buffer. It may further include other materials desirable from a commercial and user standpoint, including other buffers, diluents, filters, needles, syringes, and package inserts with instructions for performing any methods described herein.

In other aspects, the kits may be used for any of the methods described herein, including, for example, to treat an individual with one or more conditions responsive to the parent drug, or to suppress one or more such conditions.

In certain embodiments the kits may include a dosage amount of at least one formulation as disclosed herein. Kits may also comprise a means for the delivery of the formulation thereof.

The kits may include additional pharmaceutical agents for use in conjunction with the formulation described herein. In some variations, the additional pharmaceutical agent(s) may be one or more drug(s) used for treating the same disease or condition as the parent drug. These agents may be provided in a separate form, or mixed with the compounds of the present invention, provided such mixing does not reduce the effectiveness of either the pharmaceutical agent or formulation described herein and is compatible with the route of administration. Similarly the kits may include additional agents for adjunctive therapy or other agents known to the skilled artisan as effective in the treatment or prevention of the conditions described herein.

The kits may optionally include appropriate instructions for preparation and/or administration of a formulation comprising a carbonate prodrug of the invention. Information detailing possible side effects of the formulation, and any other relevant information may also be enclosed. The instructions may be in any suitable format, including, but not limited to, printed matter, videotape, computer readable disk, optical disc or directions to internet-based instructions.

In another aspect of the invention, kits for treating an individual who suffers from or is susceptible to the disease or conditions described herein are provided, comprising a first container comprising a dosage amount of a composition as disclosed herein, and instructions for use. The container may be any of those known in the art and appropriate for storage and delivery of intravenous formulation. In certain embodiments the kit further comprises a second container comprising a pharmaceutically acceptable carrier, diluent, adjuvant, etc. for preparation of the formulation to be administered to the individual.

Kits may also be provided that contain sufficient dosages of the compounds described herein (including formulations thereof) to provide effective treatment for an individual for an extended period, such as 1-3 days, 1-5 days, a week, 2 weeks, 3, weeks, 4 weeks, 6 weeks, 8 weeks, 3 months, 4 months, 5 months, 6 months, 7 months, 8 months, 9 months or morn.

The kits may include the composition as described herein packaged in either a unit dosage form or in a multi-use form. The kits may also include multiple units of the unit dose form.

Method of Treatment

The carbonate prodrugs of the present invention (e.g., a prodrug of formula (IV) or a carbonate prodrug as described herein of any one of the parent drugs selected from the group (I), (II), or (III)) may be used to treat a disease or condition that is responsive to the parent drug (e.g., pain and/or fever). In one embodiment, the invention provides a method of treating a disease or condition that is responsive to the parent drug comprising administering to an individual an effective amount of a carbonate prodrug. In some embodiments, the individual is at risk of developing a disease or condition that is responsive to the parent drug.

In some embodiments are provided methods of treating pain, fever, inflammation, ischemic injury (e.g., myocardial and/or cerebral), or neuronal injury in an individual, comprising administering to the individual an effective amount of a carbonate prodrug (e.g., (4-acetamidophenyl carbonic) phosphoric anhydride). The methods may employ prodrugs whose parent drug is an analgesic (e.g., prodrugs comprising an acetaminophen moiety). In one variation, the individual is post-operative and has or is believed to have or developed post-operative pain. In one variation, the prodrug is administered prophylactically for post-operative pain. In one variation, the individual is not amenable to oral administration of acetaminophen.

In some embodiments, such as when the parent drug of a prodrug detailed herein is an analgesic (e.g., acetaminophen) the invention embraces methods of treating pain of any etiology, including acute and chronic pain (and, for example, any pain in which acetaminophen and/or an opioid is prescribed) using a carbonate prodrug of the current invention (e.g., (4-acetamidophenyl carbonic) phosphoric anhydride). Examples of pain include post-surgical pain, post-operative pain (including dental pain), migraine, headache and trigeminal neuralgia, pain associated with burn, wound or kidney stone, pain associated with trauma (including traumatic head injury), neuropathic pain (e.g., peripheral neuropathy and post-herpetic neuralgia), pain associated with musculo-skeletal disorders, strains, sprains, contusions, fractures, such as myalgia, rheumatoid arthritis, osteoarthritis, cystitis, pancreatitis, inflammatory bowel disease, ankylosing spondylitis, sero-negative (non-rheumatoid) arthropathies, non-articular rheumatism and peri-articular disorders, and pain associated with cancer (including "break-through pain" and/or pain associated with terminal cancer). Examples of pain with an inflammatory component (in addition to some of those described above) include rheumatic pain, pain associated with mucositis, and dysmenorrhea. In some variations, the methods and formulations of the present invention are used for treatment or prevention of post-surgical pain and cancer pain. In some variations, the methods and compositions of the present invention are used for treatment or prevention of pain that is selected from the group consisting of pain associated with surgery, trauma, osteoarthritis, rheumatoid arthritis, lower back pain, fibromyalgia, postherpetic neuralgia, diabetic neuropathy. HIV-associated neuropathy and complex regional pain syndrome.

In some variations, the methods and compositions of the present invention (e.g., (4-acetamidophenyl carbonic) phosphoric anhydride) are used for treatment or prevention of pain and/or fever (e.g., in adults, children and/or infants). In some embodiments, the methods and compositions of the present invention (e.g., (4-acetamidophenyl carbonic) phosphoric anhydride) are used for treatment of pain, such as acute pain (e.g., acute pain following surgery, such as orthopedic surgery of adults, children, and/or infants). In some embodiments, the methods and compositions of the present invention (e.g., (4-acetamidophenyl carbonic) phosphoric anhydride) are used for treatment or prevention of fever, such as endotoxin-induced fever (e.g., endotoxin-induced fever in adults, children, and/or infants). In some embodiments, the methods and compositions of the present invention (e.g., (4-acetamidophenyl carbonic) phosphoric anhydride) are used for treatment or prevention of fever in children and/or infants. In some embodiments, the fever is selected from low-grade fever, moderate fever, high-grade fever and hyperpyrexia fever. In some embodiments, the fever is selected from Pel-Ebstein fever, continuous fever, intermittent fever, and remittent fever. Such methods may employ a prodrug whose parent drug is an analgesic (e.g., acetaminophen).

In some embodiments, the invention embraces methods of delaying the onset of parent drug action in an individual in need of parent drug therapy, the method comprising administering to the individual an effective amount of a carbonate prodrug of the parent drug wherein the prodrug provides a slower onset of parent drug action as compared to the parent drug. In one variation, administration of the prodrug delays the onset of parent drug action by greater than about 5 minutes, or 10 minutes, or 15 minutes, or 30 minutes, or 1 hour, or 2, hours, or 3 hours, or 4 hours, or 6 hours, or 8 hours, or 10 hours, or 12 hours, or 18 hours, or 24 hours as compared to administration of the parent drug. In some embodiments, the invention embraces little or no delay in the onset of the parent drug.

In some embodiments, the invention embraces methods of prolonging parent drug activity in an individual in need of parent drug therapy, the method comprising administering to the individual an effective amount of a carbonate prodrug of the parent drug wherein the prodrug provides prolonged parent drug activity as compared to the parent drug. In one variation, administration of the prodrug prolongs activity by greater than about 5 minutes, or 10 minutes, or 15 minutes, or 30 minutes, or 1 hour, or 2, hours, or 3 hours, or 4 hours, or 6 hours, or 8 hours, or 10 hours, or 12 hours, or 18 hours, or 24 hours as compared to administration of the parent drug. In some embodiments, the invention embraces little or no prolonging of activity compared to administration of the parent drug.

In some embodiments, the invention embraces a method of providing a drug to an individual, the method comprising administering a prodrug (e.g., a prodrug of formula IV), wherein the prodrug converts to a parent drug (e.g., acetaminophen). Also provided are methods of providing a drug to an individual by administering a prodrug (e.g., a prodrug of formula IV), where the prodrug converts to the drug (e.g., acetaminophen) in vivo. In one aspect, the prodrug (e.g., a prodrug of formula IV) results in conversion to the drug (e.g., acetaminophen) within about 1, 5, 10, 15, or 30 min following administration. Conversion may be measured by techniques known in the art, including those detailed in the Experimental section herein. In some embodiments, the invention embraces methods of providing a drug to an individual (e.g., an individual in need thereof), the method comprising administering to the individual an effective amount of a prodrug (e.g., a prodrug of formula (IV) or a carbonate prodrug as described herein of any one of the parent drugs selected from the group (I), (II), or (III)) wherein greater than about any of 10%, or 15%, or 20%, or 25%, or 30%, or 35%, or 40%, or 45%, or 50%, or 60%, or 75% or 85%, or 90%, or 95% of the prodrug is converted to parent drug (e.g., acetaminophen) after less than about any of 1 min, 3 min, 5 min, 10 min, 20 min, or 30 min, or 45 min, or 1 hr following administration. In some embodiments, the method comprises administering to the individual an effective amount of a prodrug (e.g., a prodrug of formula IV) wherein greater than about 45% or about 60% of the prodrug is converted to the parent drug (e.g., acetaminophen) after less than about 1 min or about 3 min following administration.

In some embodiments, the invention embraces a method of providing a drug to an individual (e.g., an individual in need thereof), the method comprising administering to the individual (e.g., intravenously) an effective amount of a prodrug (e.g., a prodrug of formula (IV) or a carbonate prodrug as described herein of any one of the parent drugs selected from the group (I), (H), or (III)) wherein the resulting concentration of the parent drug (e.g., acetaminophen) or a metabolite thereof at about any of 10 min, or 20 min, or 30 min, or 45 min, or 1 hr, or 2 hr, or 3 hr following administration is within less than about any of 50%, or 40%, or 30%, or 25%, or 20%, or 15%, or 10%, or 5% when compared to the administering the parent drug alone under the same conditions. For example, in some embodiments, methods of providing a drug to an individual in need thereof are provided, the methods comprising intravenously administering to the individual an effective amount of a prodrug (e.g., a prodrug of formula IV) wherein the resulting concentration of the parent drug or metabolite thereof (e.g., acetaminophen) at about 30 min or 1 hr following administration is within less than about 15% or about 5% when compared to administering the parent drug (e.g., acetaminophen) alone under the same conditions.

Combination Therapy

The carbonate prodrugs of the present invention may be formulated and/or administered in conjunction with one or more additional pharmaceutical agents, as described herein and as known in the art, including one or more additional pharmaceutical agents to further reduce the occurrence and/or severity of symptoms and/or clinical manifestations thereof, as well as additional pharmaceutical agents that treat or prevent the underlying conditions, or in conjunction with (e.g., prior to, concurrently with, or after) additional treatment modalities. The carbonate prodrugs as described herein may be administered before, concurrently with, or after the administration of one or more of the additional pharmaceutical agents. The carbonate prodrugs described herein may also be administered in conjunction with (e.g., prior to, concurrently with, or after) agents to alleviate the symptoms associated with either the condition or the treatment regimen.

In one variation, a carbonate prodrug of the current invention may be formulated and/or administered with its corresponding parent drug. Such combination therapy may provide an initial therapeutic amount of the parent drug, followed by a delayed and/or prolonged parent drug activity. For example, a combination of (4-acetamidophenyl carbonic) phosphoric anhydride with acetaminophen may provide an initial treatment of pain with acetaminophen, followed by prolonged treatment of pain with the acetaminophen prodrug. Such formulations may permit a decreased dosing frequency.

In some embodiments of the formulations and methods of the present invention, the carbonate prodrugs are used in combination with one or more additional pharmaceutical agents. The additional pharmaceutical agent is an agent other than the parent drug moiety being used. Representative additional pharmaceutical agents include opioids (natural, semi-synthetic, or synthetic), non-steroidal anti-inflammatory drugs (NSAIDs), benzodiazepines, barbiturates and other compounds, such as caffeine. Examples of compounds contemplated for combination with prodrug of current invention include, but are not limited to, codeine, morphine, hydrocodone, hydromorphone, levorphanol, propoxyphene, aspirin, ketorolac, ibuprofen, ketoprofen, flurbiprofen, etodolac, diclofenac, misoprostol, meloxicam, piroxicam, naproxen, caffeine, tramadol, doxylamine, pamabrom, dextropropoxyphene, methythexital, carisoprodol, butalbital diazepam, lorazepam, and midazolam. One potential advantage of combination formulation is that the formulation may induce analgesia beyond the ceiling effect of acetaminophen without necessity to approach the toxic or nearly toxic dose levels of acetaminophen. Combinations of the acetaminophen prodrugs with benzodiazepines such as diazepam, lorazepam, midazolam or any other benzodiazepines, may be used for treatment of pre- and postoperative anxiety in addition to the treatment of e.g., analgesia. Such combination may be particularly useful in dental surgeries (e.g., mole extraction).

In some embodiments, the carbonate prodrugs (e.g. a compound of formula (IV) or a prodrug of the a parent drug selected from group (I), (II), or (III), or a pharmaceutically acceptable salt thereof or solvate of the foregoing) are used in combination with one or more additional pharmaceutical agents selected from group (I), (II), or (III), or a pharmaceutically acceptable salt thereof or solvate of the foregoing.

The above additional pharmaceutical agents to be employed in combination with the carbonate prodrugs of the invention may be used in therapeutic amounts, such as those indicated in the PHYSICIANS' DESK REFERENCE (PDR) 53rd Edition (1999), or such therapeutically useful amounts as would be known to one of ordinary skill in the art.

Additional pharmaceutical agents administered with one or more of the carbonate prodrugs of the present invention can be administered at the recommended maximum clinical dosage or at lower doses. Dosage levels of the additional pharmaceutical agents in the formulations of the invention may be varied so as to obtain a desired therapeutic response depending on the route of administration, severity of the disease and the characteristics and response of the patient. The combination can be administered as separate formulations or as a single dosage form containing both agents. When administered as a combination, the carbonate prodrugs can be formulated as separate formulations, which are given at the same time or different times, or the prodrugs, can be given as a single formulation.

As will be well appreciated by the skilled artisan, for particular conditions, different additional pharmaceutical agent(s) and/or additional treatment modality(ies) may be employed.

The formulations and methods of the carbonate prodrugs described herein may be used alone or in conjunction with (e.g., prior to, concurrently with, or after) other modes of treatments (e.g., adjunctive therapy with additional pharmaceutical agents described herein with reference to pharmaceutical formulations of the claimed compounds or known to the skilled artisan) used to treat or prevent the condition being treated/prevented and/or administration of an additional treatment modality, or combinations of the foregone). For example, in combination with one or more additional pharmaceutical agents as described herein and known to those of skill in the art and/or currently available treatment modalities, including, for example, surgery or radiotherapy. As used herein, the term "additional treatment modality" refers to treatment/prevention of the conditions described herein without the use of a pharmaceutical agent (e.g., surgery, radiotherapy, etc.). Where combinations of pharmaceutical agent(s) and/or additional treatment modality(ies) are used, they may be, independently, administered prior to, concurrently with, or after administration of one or more of the carbonate prodrugs (or formulation(s) thereof) as described herein.

The optimal combination of one or more additional treatment modalities and/or additional pharmaceutical agents in conjunction with administration of the formulations described herein, can be determined by an attending physician or veterinarian based on the individual and taking into consideration the various factors effecting the particular individual, including those described herein.

Dosing and Methods of Administration

The carbonate prodrugs of the present invention and formulations described herein will generally be used in an amount effective to achieve the intended result, for example in an effective amount to treat or prevent the particular condition being treated or prevented (e.g., pain and/or fever). The amount of the prodrug or formulation administered in order to administer an effective amount will depend upon a variety of factors, including, for example, the particular condition being treated, the frequency of administration, the particular formulation being administered, the severity of the condition being treated and the age, weight and general health of the individual, the adverse effects experienced by the individual being treated, etc. Determination of an effective dosage is within the capabilities of those skilled in the art, particularly in view of the teachings provided herein. Dosages may also be estimated using in vivo animal models.

The amount of carbonate prodrug of the present invention that may be combined with the carrier materials to produce a single dosage form may vary depending upon the host to which the prodrug is administered and the particular mode of administration, in addition to one or more of the variety of factors described above. A pharmaceutical unit dosage chosen may be fabricated and administered to provide a defined final concentration of drug in the blood, tissues, organs, or other targeted region of the body. The effective amount for a given situation can be readily determined by routine experimentation and is within the skill and judgment of the ordinary clinician.

In some embodiments, toxic dosage (e.g., $LD_{50}$ or NOAEL (No Observed Adverse Effect Level)) of a carbonate prodrug of the present invention may be higher than the molar equivalent toxic dosage of the parent drug. In some embodiments, the toxic dosage of the carbonate prodrug is 1.2, 2, 5, 7.5, 10, 15, 20, 50, 100, 250, 500, or 1000 times higher than parent drug.

In some embodiments, the dosage of the carbonate prodrug required to obtain the same blood level concentration as the parent drug is lower due to the increased solubility of the prodrug. In some embodiments, the required dosage of the carbonate prodrug to obtain the same blood level concentration as the parent drug is 1.2, 2, 5, 7.5, 10, 15, 20, 50, or 100 times lower than parent drug.

Examples of carbonate prodrug dosages (e.g., alone or in combination with an additional pharmaceutical agent) which can be used are an effective amount within the dosage range of about 0.1 µg/kg to about 300 mg/kg, or within about 1.0 µg/kg to about 40 mg/kg body weight, or within about 1.0 µg/kg to about 20 mg/kg body weight, or within about 1.0 µg/kg to about 10 mg/kg body weight, or within about 10.0 µg/kg to about 10 mg/kg body weight, or within about 100 µg/kg to about 10 mg/kg body weight, or within about 1.0 mg/kg to about 10 mg/kg body weight, or within about 10 mg/kg to about 100 mg/kg body weight, or within about 50 mg/kg to about 150 mg/kg body weight, or within about 100 mg/kg to about 200 mg/kg body weight, or within about 150 mg/kg to about 250 mg/kg body weight, or within about 200 mg/kg to about 300 mg/kg body weight, or within about 250 mg/kg to about 300 mg/kg body weight. Other dosages which can be used are about 0.01 mg/kg body weight, about 0.1 mg/kg body weight, about 1 mg/kg body weight, about 10 mg/kg body weight, about 20 mg/kg body weight, about 30 mg/kg body weight, about 40 mg/kg body weight, about 50 mg/kg body weight, about 75 mg/kg body weight, about 100 mg/kg body weight, about 125 mg/kg body weight, about 150 mg/kg body weight, about 175 mg/kg body weight, about 200 mg/kg body weight, about 225 mg/kg body weight, about 250 mg/kg body weight, about 275 mg/kg body weight, or about 300 mg/kg body weight. Compounds of the present invention may be administered, alone or in combination, in a single daily dose, or the total daily dosage may be administered in divided dosage of two, three, four, five, or six times daily.

The frequency and duration of administration of the carbonate prodrug will depend on the condition being treated, the condition of the individual, and the like. The formulation may be administered to the individual one or more times, for example, 2, 3, 4, 5, 10, 15, 20, or more times. The formulation may be administered to the individual, for example, more than, equal to, or less than once a day, 2 times a day, 3 times a day, or more than 3 times a day; or 1-6 times a day, 2-6 times a day, or 4-6 times a day. The formulation may also be administered to the individual, for example, less than once a day, for example, every other day, every third day, every week, or less frequently. The formulation may be administered over a period of days, weeks, or months.

The carbonate prodrugs of the invention may be administered enterally (e.g., orally or rectally), parenterally (e.g., by injection (such as intravenously, subcutaneously or intramuscularly), or by inhalation (e.g., as mists or sprays)), or topically, in dosage unit formulations containing conventional nontoxic pharmaceutically acceptable carriers, adjuvants, and vehicles as desired. For example, suitable modes of administration include oral, subcutaneous, transdermal, transmucosal, iontophoretic, intravenous, intraarterial, intramuscular, intraperitoneal, intranasal (e.g., via nasal mucosa), subdural, rectal, gastrointestinal and the like, and directly to a specific or affected organ or tissue. For delivery to the central nervous system, spinal and epidural administration, or administration to cerebral ventricles, can be used. Topical administration may also involve the use of transdermal administration such as transdermal patches or iontophoresis devices. The term parenteral as used herein includes subcutaneous injections, intravenous, intramuscular, intrasternal injection, or infusion techniques. The prodrugs may be mixed with pharmaceutically acceptable carriers, adjuvants, and vehicles appropriate for the desired route of administration. The route of administration may vary according to the condition to be treated. Additional methods of administration are known in the art.

In some embodiments of the methods, the route of administration for carbonate prodrugs of the invention is oral. In some embodiments, formulations are suitable for oral administration. The prodrugs described for use herein can be administered in solid form, in liquid form, in aerosol form, or in the form of tablets, pills, powder mixtures, capsules, granules, injectables, creams, solutions, suppositories, enemas, colonic irrigations, emulsions, dispersions, food premixes, and in other suitable forms.

Solid dosage forms for oral administration may include capsules, tablets, pills, powders, and granules. In such solid dosage forms, the active compound may be admixed with at least one inert diluent such as sucrose, lactose, or starch. Such dosage forms may also comprise additional substances other than inert diluents, e.g., lubricating agents such as magnesium stearate. In the case of capsules, tablets, and pills, the dosage forms may also comprise buffering agents. Tablets and pills can additionally be prepared with enteric coatings.

Liquid dosage forms for oral administration may include pharmaceutically acceptable emulsions, solutions, suspensions, syrups, and elixirs containing inert diluents commonly used in the art, such as water. Such formulations may also comprise adjuvants, such as wetting agents, emulsifying and suspending agents, cyclodextrins, and sweetening, flavoring, and perfuming agents.

In some embodiments, the carbonate prodrugs of the invention (e.g., (4-acetamidophenyl carbonic) phosphoric anhydride) are administered parenterally (e.g., intravenously or intramuscularly). Injectable preparations, for example, sterile injectable aqueous or oleaginous suspensions, may be formulated according to the known art using suitable dispersing or wetting agents and suspending agents. The sterile injectable preparation may also be a sterile injectable solution or suspension in a nontoxic parenterally acceptable diluent or solvent, for example, as a solution in propylene glycol. The sterile injectable preparation may also be a sterile powder to be reconstituted using acceptable vehicles prior to administration. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid may be used in the preparation of injectables.

In some embodiments are provided high doses of carbonate prodrug in a low volume (e.g., in a low volume of saline). Non-limiting examples of an effective amount (e.g., for parenteral administration, such as intravenous or intramuscular), include the prodrug (e.g., (4-acetamidophenyl carbonic) phosphoric anhydride) at a dosage range of from about 20 mg per day to about 8 g per day, or from about 60 mg per day to about 6 g, or from about 200 mg per day to about 4 g, or from about 300 mg to about 2.6 g per day, or from about 500 mg to about 2 g per day. In some embodiments, the effective amount for parenteral (e.g., intravenous or intramuscular) administration is a dose range about of about 0.01 µmol to about 100 mmol, or about 0.1 µmol to about 75 mmol, or about 0.5 µmol to about 50 µmol, or about 1 µmol to about 50 mmol, or about 5 µmol to about 50 mmol, or about 10 µmol to about 25 mmol, or about 100 µmol to about 10 mmol, or about 500 µmol to about 5 mmol, or about 0.01 mg to about 20 g, or about 0.1 mg to about 20 g, or about 0.5 mg to about 15 g, or about 1 mg to about 15 g, or about 2 mg to about 10 g, or about 5 mg to about 10 g, or about 10 mg to about 10 g, or about 50 mg to about 7.5 g, or about 100 mg to about 7.5 g, or about 200 mg to about 5 g, or about 500 mg to about 4 g, or about 750 mg to about 3 g, or about 1 g to about 2.5 g, or about 1.3 g to about 1.9 g, and may be administered in about 1 mL to about 1000 mL, or about 1 mL to about 500 mL, or about 1 mL to about 100 mL, or about 1 mL to about 50 mL, about 1 mL to about 30 mL, or about 1 mL to about 25 mL, or about 5 mL to about 20 mL, or about 5 mL to about 15 mL or about 10 mL to about 15 mL, or about 5 mL to about 10 mL. In some of these embodiments, the prodrug (e.g., (4-acetamidophenyl carbonic) phosphoric anhydride) is administered in a solution at a concentration of about 10 mg/mL to about 1000 mg/mL, or about 25 mg/mL to about 750 mg/mL, or about 50 mg/mL to about 500 mg/mL, or about 75 mg/mL to about 400 mg/mL, or about 100 mg/mL to about 300 mg/mL, or about 150 mg/mL to about 250 mg/mL.

The invention also includes formulations of carbonate prodrugs administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

The carbonate prodrugs of the invention may also be administered in the form of liposomes. As is known in the art, liposomes are generally derived from phospholipids or other lipid substances. Liposomes are formed by mono- or multilamellar hydrated liquid crystals that are dispersed in an aqueous medium. Any non-toxic, physiologically acceptable and/or metabolizable lipid capable of forming liposomes may be used. The present formulations in liposome form can contain, in addition to a prodrug, stabilizers, preservatives, excipients, and the like. In some embodiments, the lipids are the phospholipids and/or phosphatidyl cholines (lecithins), natural and/or synthetic. Methods to form liposomes are known in the art. See, for example, Prescott, Ed., *Methods in Cell Biology*, Volume XIV, Academic Press, New York, N.W., p. 33 et seq (1976).

EXAMPLES

The present invention will be understood more readily by reference to the following examples, which are provided by way of illustration and are not intended to be limiting of the present invention.

Example 1: Synthesis of (4-acetamidophenyl carbonic) phosphoric anhydride 4-acetamidophenyl carbonochloridate

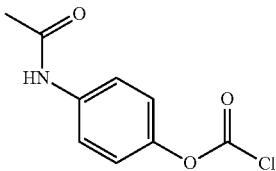

A solution of 4-acetominophenol (75.0 g), phosgene solution (450 mL, 20% in toluene), and ethyl acetate (1875 mL) was cooled to 0° C. N,N-Diethylaniline (94.7 mL) was added dropwise and the reaction was stirred at 0° C. for two hours. The reaction was then allowed to warm to room temperature. An aliquot for NMR analysis was taken four hours post addition. The reaction remained incomplete and was stirred at room temperature overnight. An-aliquot for NMR analysis after overnight stirring indicated no change had occurred in the reaction since the previous aliquot. The reaction was heated to 40° C. until phosgene gas evolution ceased (approximately 30 minutes). The reaction was cooled to room temperature and was then filtered. The filter cake was washed with ethyl acetate. NMR analysis of the filtered solid indicated it was N, N-diethylaniline related material. The filtrate was washed was washed with 0.1N HCl (375 mL). The organic layer was dried over sodium sulfate, filtered, and concentrated in vacuo to afford a pale yellow solid. The solid was triturated using ether (375 mL) for twenty minutes at room temperature. The solid was filtered and washed with ether. NMR analysis indicated product with residual ether remaining. The solid was dried overnight in a vacuum oven at ambient temperature to afford 77.55 g (73.3% yield). NMR and MS analysis indicated product. $^1$H NMR (300 MHz, CDCl$_3$+DMSO-d6): δ 9.18 (s, 1H), 7.62 (d, 2H), 7.15 (d, 2H), 2.18 (s, 3H); MS m/z: 214 (M+H)$^+$.

di-tert-butyl hydrogen phosphate

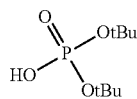

A solution of di-tert-butyl phosphite (175 g), potassium bicarbonate (54.2 g), and deionized water (788 mL) was cooled to 0° C. Potassium permanganate (99.7 g) was divided into three equal portions of 33.2 g and each portion was added over one hour. During the addition, the maximum temperature observed was 21.6° C. Once the addition was complete, the reaction was allowed to warm to room temperature and was stirred for thirty minutes. Decolorizing carbon (13.4 g) was added and the reaction was heated to 60° C. for fifteen minutes. The suspension was filtered (very slowly) and washed with deionized water (250 mL). The filtrate was again heated to 60° C. with decolorizing carbon (22.4 g) for 20 min. The suspension was filtered and the filter cake was washed with deionized water (250 mL). The filtrate was cooled to 0° C. in an ice/water bath. The pH of the solution was 8-9. Concentrated HCl (157.2 mL) was added to acidify the solution to pH=1. A white precipitate immediately formed. The slurry was continued to stir at 0° C. for ten minutes. The white solid was filtered and washed with cold deionized water (219 mL). The tilter cake was dissolved in chloroform (500 mL) and was dried over sodium sulfate. The dried solution was filtered, washed with chloroform, and concentrated in vacuo to afford a white solid (87.4 g, 46.2% yield). NMR analysis indicated pure product. $^1$H NMR (300 MHz): δ 1.45 (s, 18H); $^{31}$P NMR (121 MHz): δ −604.30.

(4-acetamidophenyl carbonic) (di-tert-butyl phosphoric) anhydride

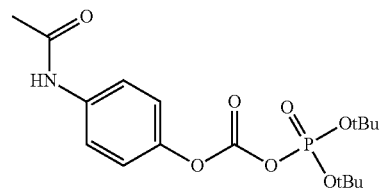 [SMILES: CC(=O)Nc1ccc(OC(=O)OP(=O)(OC(C)(C)C)OC(C)(C)C)cc1]

A solution of di-tert-butyl phosphate (100.3 g) was dissolved in chloroform (1530 mL) and cooled to 0° C. followed by the addition of triethylamine (33.2 mL). An exotherm to 8.6° C. was observed. 4-acetamidophenyl carbonochloridate (51 g) was added to the reaction portion-wise (17 g every five minutes). Following addition, the reaction was allowed to warm to room temperature. Aliquots for NMR analysis were taken after 50, 80, 120 minutes post addition. The reaction appeared complete after 2 h. The reaction was washed with deionized water (3092 mL) and thrice with 5% citric acid trisodium dihydrate (2068 mL each). The organic layer was dried over sodium sulfate, filtered, and concentrated in vacuo at ambient temperature to afford an off-white solid. NMR analysis indicated a 20% impurity. The solid was dissolved in methylene chloride (500 mL) and was washed with 1N NaOH (500 mL). The organic layer was dried over sodium sulfate, filtered, and concentrated in vacuo at ambient temperature. The resulting off-white solid (71.9 g; 77.4% yield) was identified as a product by NMR analysis. $^1$H NMR (300 MHz): δ 8.80 (s, 1H), 7.62 (d, 2H), 7.15 (d, 2H), 2.18 (s, 3H), 1.58 (s, 18H); $^{31}$P NMR (121 MHz): δ −2226.10.

(4-acetamidophenyl carbonic) phosphoric anhydride

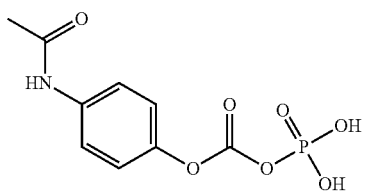 [SMILES: CC(=O)Nc1ccc(OC(=O)OP(=O)(O)O)cc1]

A suspension of (4-acetamidophenyl carbonic) (di-tert-butyl phosphoric) anhydride (17.5 g). TFA (67.2 mL), and acetic acid (100.8 mL) was stirred at room temperature. The reaction quickly became homogenous and a precipitate formed within 20 minutes post addition. Aliquots for NMR analysis taken after 15 and 30 minutes stirring confirmed reaction completion. The slurry was poured into MTBE (1750 mL) and stirred for 15 minutes at room temperature. The MTBE was dried overnight using magnesium sulfate. The solid was filtered through a 250-mL nitrogen-pressured funnel (Praxair 5.0 Ultra High Purity Grade Nitrogen). The white filter cake was washed with MTBE (350 mL). The solid was dried for two hours under nitrogen in the funnel, then transferred to a crystal flesh and continued-to dry for an additional 2.5 hours under nitrogen. The resulting white solid (7.15 g, 57.5% yield) was approximately 97.9% wt. pure product by NMR analysis (acetaminophen (2.0% wt) and MTBE (0.1% wt, 1000 ppm)). $^1$H NMR (300 MHz, DMSO-d6): δ 10.05 (s, 1H), 7.61 (d, 2H), 7.19 (d, 2H), 2.05 (s, 3H); $^{31}$P NMR (121 MHz): δ −997.96.

Example 2: Carbonate Prodrug Solubility: (4-acetamidophenyl carbonic) phosphoric anhydride Solubility of the prodrug (4-acetamidophenyl carbonic) phosphoric anhydride was determined in water, glycerol, and propylene glycol. 10 mg of (4 acetamidophenyl carbonic) phosphoric anhydride was weighed into a vial, small amounts of solvent were added and the mixture was sonicated until a solution formed.

9.9 mg (4-acetamidophenyl carbonic) phosphoric anhydride dissolved in 65 μL water=152 mg/mL.

10 mg (4-acetamidophenyl carbonic) phosphoric anhydride dissolved in 0.608 g glycerol=20.6 mg/mL (glycerol d=1.25 g/mL).

10.1 mg (4-acetamnidophenyl carbonic) phosphoric anhydride dissolved in 65.6 mg propylene glycol=154 mg/mL (propylene glycol d=1.036 g/mL).

Example 3: Carbonate Prodrug Stability in D$_2$O: (4-acetamidophenyl carbonic phosphoric anhydride (4-acetamidophenyl carbonic) phosphoric (29.5 mg) was dissolved in D$_2$O (0.7 mL) and monitored by proton NMR. The integration of peaks at 7.8 ppm (corresponding to (4-acetamidophenyl carbonic) phosphoric) and 6.9 ppm (corresponding to acetaminophen) were compared. The half-life of (4-acetamidophenyl carbonic) phosphoric under these conditions was found to be about 90 minutes. The data are summarized in Table 1.

TABLE 1

(4-acetamidophenyl carbonic) phosphoric anhydride in water at room temperature

| Time (min) | Remaining Prodrug |
|---|---|
| 3 | 94.4% |
| 9 | 90.3% |
| 14 | 86.4% |
| 29 | 75.7% |
| 39 | 70.9% |
| 49 | 65.6% |
| 60 | 61.0% |
| 75 | 55.5% |
| 90 | 50.6% |
| 105 | 46.0% |
| 120 | 41.7% |
| 146 | 36.7% |
| 188 | 29.3% |
| 270 | 20.2% |
| 375 | 13.9% |
| 420 | 11.7% |
| 495 | 8.4% |
| 840 | 3.0% |
| 1410 | 1.4% |

Example 4: Carbonate Prodrug Stability in Propylene Glycol-d$_8$: (4-acetamidophenyl carbonic) phosphoric anhydride (4-acetamidophenyl carbonic) phosphoric anhydride (20.4 mg) was dissolved in 600 mg propylene glycol-ds and $^1$H and $^{31}$P NMR spectra were recorded at room temperature. In addition to (4-acetamidophenyl carbonic) phosphoric anhydride (d −766 ppm), there were peaks at d +334, 265 (likely H$_3$PO$_4$) and +203 ppm. The half-life of (4-acetamidophenyl carbonic) phosphoric anhydride under these conditions was found to be about 6.3 hours. The data are summarized in Table 2:

TABLE 2

(4-acetamidophenyl carbonic) phosphoric anhydride in Propylene Glycol-d$_8$ at room temperature

| Time (min) | Remaining Prodrug | |
|---|---|---|
| | $^1$H NMR | $^{31}$P NMR |
| 10 | 94.03% | 96.7% |
| 18 | 92.64% | 94.5% |
| 78 | 90.79% | 92.1% |
| 41 | 88.57% | 89.9% |
| 51 | 86.84% | 88.4% |
| 61 | 85.36% | 86.4% |
| 70 | 83.93% | 85.0% |
| 120 | 74.63% | 77.6% |
| 169 | 68.80% | 71.7% |
| 228 | 62.97% | 64.9% |
| 297 | 56.82% | 57.4% |
| 345 | 52.10% | 57.8% |
| 380 | 49.13% | 49.6% |
| 425 | 46.33% | 46.6% |
| 446 | 45.67% | 44.0% |
| 1269 | 19.61% | 17.1% |

Example 5: Carbonate Prodrug Stability in Propylene Glycol-d$_8$ at low temperature (4-acetamnidophenyl carbonic) phosphoric anhydride Two samples of (4-acetamidophenyl carbonic) phosphoric anhydride (20 mg each) were dissolved in propylene glycol-ds (600 mg) and the samples were stored at 4° C. and −20° C. The samples were examined periodically by $^1$H NMR for the formation of acetaminophen as a measure of stability. The amounts of acetaminophen formed at 4° C. and −20° C. are reported and summarize in Table 3. As shown in the table, low temperature storage improved the stability of the prodrug.

TABLE 3

(4-acetamidophenyl carbonic) phosphoric anhydride in Propylene Glycol-d$_8$ at low Temperature

| Time (h) | Acetaminophen Formation | |
|---|---|---|
| | 4° C. | −20° C. |
| 0.17 | 7.1% | 10.1% |
| 19.3 | 37.8% | 15.0% |
| 44.5 | 58.5% | 20.5% |
| 68.7 | 71.5% | 25.0% |
| 94.0 | 79.3% | 29.0% |
| 116 | 83.1% | 32.2% |
| 140 | 84.6% | 36.2% |

Example 6: In Vitro Conversion of Acetaminophen Prodrug to Acetaminophen

Figure 2:
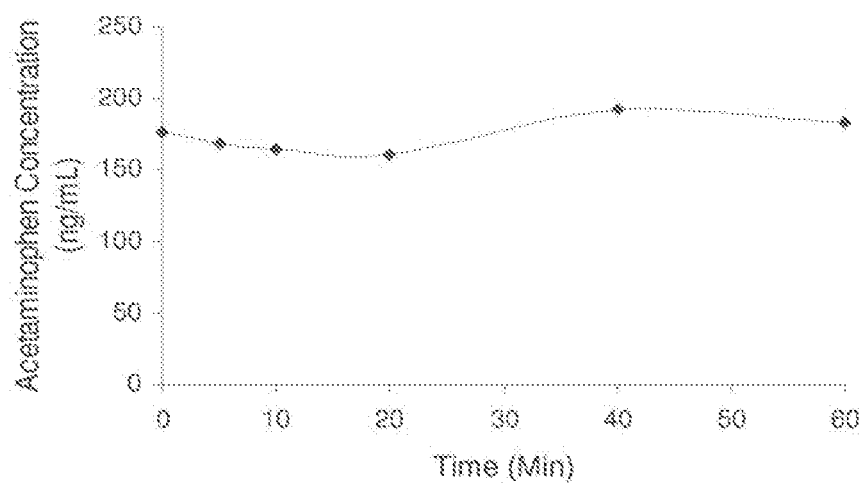
FIG. 2 shows data for the formation of acetaminophen from 0.3 μg/mL of the compound of formula (IV) in human plasma.

A known amount of (4-acetamidophenyl carbonic) phosphoric anhydride was incubated with human plasma samples maintained at physiological temperature. Small aliquots were drawn at predefined time points (0, 5, 10, 15, 20, 25, 30, 40, 60 and 120 minutes) and analyzed for acetaminophen content. The experiment was performed with two different concentrations of prodrug (15 μg/mL and 0.3 μg/mL) in pooled human plasma at 37° C. to determine kinetics of metabolic reaction and whether or not saturation of enzymatic system involved in conversion of prodrug to acetaminophen drug takes place. It was found that acetaminophen appeared by the time of first sample collection at nominal 0 minutes, and the concentration gradually decreased over the duration of 60 minutes, as shown in FIGS. 1 and 2.

Example 7: In Vivo Conversion of Acetaminophen Prodrug to Acetaminophen

Conversion of acetaminophen prodrug to acetaminophen through metabolism in the body was studied in rats. Similar to experimental design described above for in vitro studies, the compound of formula (IV) was intravenously administered to the test animal and blood is drawn at predefined time points. The blood was analyzed for acetaminophen content, and the half-life of prodrug was determined.

Figure 3:
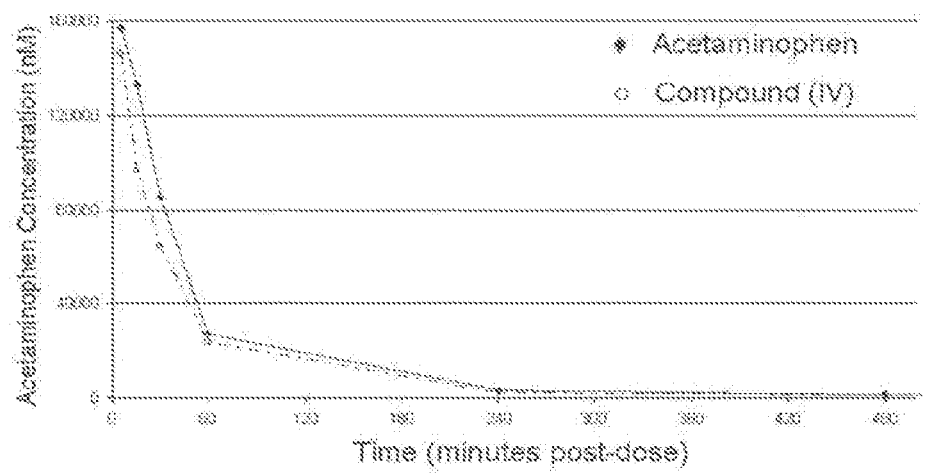
FIG. 3 shows the time-dependent plasma concentration of acetaminophen from the compound of formula (IV) compared to the parent drug acetaminophen.

The pharmacokinetics of acetaminophen and the compound of formula (IV) were evaluated after intravenous (IV) administration to determine resulting plasma acetaminophen concentrations. Acetaminophen and the compound of formula (IV) were dosed on an equimolar basis to provide the same level of exposure (25 mg/kg) to acetaminophen and to obtain the profile of compound (IV) conversion in vivo to acetaminophen. The test animals were male and female Sprague Dawley (CD® IGS) rats (Charles River Laboratories), 7 to 8 weeks of age, weighing 220 to 270 grams. The rats were serially bled at 7 time points: 5, 15, 30 minutes and 1, 4, 8 and 24 hours post-dose. Whole blood samples (300 μL) were collected from the vein in lithium heparin microcontainers, processed to plasma by centrifugation and plasma was stored frozen at −70° C. until analyzed. Results of plasma analyses for acetaminophen contents are shown in FIG. 3 and Table 4.

TABLE 4

Summary of calculated pharmacokinetic parameters of acetaminophen after intravenous administration of Compound (IV) to rats

| PK Parameter | Acetaminophen | | Compound (IV) | |
|---|---|---|---|---|
| | Mean | % CV | Mean | % CV |
| Dose (mg/kg) | 25 | N.A. | 25* | N.A. |
| Half life (hr) | 2.65 | 43.7 | 3.14 | 26.5 |
| T$_{max}$ (hr) | 0.139 | 62.2 | 0.083 | 0.00** |
| C$_{max}$ (ng/mL) | 26467 | 22.8 | 25983 | 16.1 |
| AUC$_{0-8}$ (hr · ng/mL) | 24300 | 33.6 | 27833 | 69.2 |
| Clearance (mL/min/kg) | 19.5 | 40.5 | 19.7 | 46.1 |
| V$_{ss}$ (L/kg) | 1.48 | 25.0 | 1.73 | 45.8 |

*molar equivalent of 25 mg/kg acetaminophen;
**all values the same

What is claimed is:
1. A compound of the formula

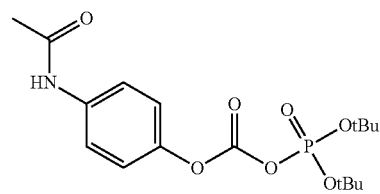 [SMILES: CC(=O)Nc1ccc(OC(=O)OP(=O)(OC(C)(C)C)OC(C)(C)C)cc1]

or a salt thereof.

* * * * *